(12) United States Patent
Nishio et al.

(10) Patent No.: US 8,721,855 B2
(45) Date of Patent: May 13, 2014

(54) CRIMP CONTACT, CRIMP CONTACT WITH AN ELECTRICAL LEAD, GAS SENSOR INCLUDING SAID CRIMP CONTACT AND METHOD FOR MANUFACTURING SAID GAS SENSOR

(75) Inventors: Hisaharu Nishio, Aichi (JP); Masahiro Asai, Aichi (JP); Makoto Hishiki, Aichi (JP)

(73) Assignee: NGK Spark Plug Co. Ltd., Aichi (JP)

( * ) Notice: Subject to any disclaimer, the term of this patent is extended or adjusted under 35 U.S.C. 154(b) by 1186 days.

(21) Appl. No.: 11/605,243

(22) Filed: Nov. 29, 2006

(65) Prior Publication Data
US 2007/0128955 A1 Jun. 7, 2007

(30) Foreign Application Priority Data
Dec. 2, 2005 (JP) ................. 2005-349407

(51) Int. Cl.
G01N 27/407 (2006.01)
(52) U.S. Cl.
USPC ........... 204/424; 204/425; 204/426; 204/427; 204/428; 439/877; 439/879; 439/878; 73/23.31; 73/23.32
(58) Field of Classification Search
USPC .......... 204/406, 421–429; 73/114.71–114.73; 205/781, 783.5, 784.5; 439/877, 878, 439/886
See application file for complete search history.

(56) References Cited

U.S. PATENT DOCUMENTS

| | | | | |
|---|---|---|---|---|
| 4,514,032 A | * | 4/1985 | Lawrence | 439/884 |
| 4,890,384 A | * | 1/1990 | Shaffer | 29/863 |
| 5,129,143 A | * | 7/1992 | Wei et al. | 29/885 |
| 5,245,132 A | * | 9/1993 | Luetzow | 174/74 R |
| 5,525,070 A | | 6/1996 | Axelsson | |

(Continued)

FOREIGN PATENT DOCUMENTS

| | | |
|---|---|---|
| CN | 1419160 A | 5/2003 |
| CN | 1656375 A | 8/2005 |

(Continued)

OTHER PUBLICATIONS

Trial Decision dated Feb. 5, 2013 for corresponding JP 2006-239638.
Japanese Office Action for corresponding Japanese Application No. 2006-239638, dated Sep. 25, 2012.

Primary Examiner — Bach Dinh
(74) Attorney, Agent, or Firm — Sughrue Mion, PLLC

(57) ABSTRACT

A crimp contact, a gas sensor including the crimp contact for outputting a signal from a sensing portion of a sensor element to an external device, and a method for manufacturing the crimp contact. The crimp contact includes a barrel portion crimped so as to fix a plurality of lead core wires (16) of an electrical lead connected to the external device. A hold portion constituting the barrel portion is formed such that the lead core wires 16 of the electrical lead are disposed in an U-shaped hold portion 77 so as to be crimped between an anvil 120 and a crimper 121. An outer surface of the U-shaped hold portion 77 has a plating layer 85 thereon to thereby constantly secure slidability between a sliding face of the crimper 121 and the outer surface of the U-shaped hold portion 77. The crimp contact is able to secure slidability between an outer surface of a hold portion and a sliding face of a crimper without applying any lubricant to the sliding face of the crimper, and can be used under a high temperature environment.

19 Claims, 17 Drawing Sheets

(56) References Cited

U.S. PATENT DOCUMENTS

| | | | |
|---|---|---|---|
| 5,561,267 A | 10/1996 | Fudoo et al. | |
| 5,762,526 A * | 6/1998 | Kuramoto et al. | 439/877 |
| 6,395,159 B2 * | 5/2002 | Matsuo et al. | 204/427 |
| 6,942,529 B2 * | 9/2005 | Fujimoto et al. | 439/886 |
| 7,461,538 B2 * | 12/2008 | Matsuo et al. | 73/23.31 |
| 7,674,143 B2 | 3/2010 | Matsuo et al. | |
| 8,156,790 B2 | 4/2012 | Matsuo et al. | |
| 2003/0128976 A1 | 7/2003 | Ichinose et al. | |
| 2004/0221634 A1 * | 11/2004 | Saito et al. | 72/17.2 |
| 2005/0145013 A1 | 7/2005 | Hayashi et al. | |
| 2007/0052862 A1 | 3/2007 | Matsuo et al. | |
| 2007/0096615 A1 | 5/2007 | Matsuo et al. | |
| 2009/0126456 A1 | 5/2009 | Matsuo et al. | |

FOREIGN PATENT DOCUMENTS

| | | |
|---|---|---|
| DE | 195 23 557 A1 | 1/1997 |
| JP | 64-41184 A | 2/1989 |
| JP | 7-176337 A | 7/1995 |
| JP | 8-167442 A | 6/1996 |
| JP | 8-321330 A | 12/1996 |
| JP | 8-511911 A | 12/1996 |
| JP | 2970362 B2 | 11/1999 |
| JP | 2000-180273 A | 6/2000 |
| JP | 2000-208231 A | 7/2000 |
| JP | 2003-59612 A | 2/2003 |
| JP | WO2005029057 * | 3/2005 |
| WO | 2005/029057 A1 | 3/2005 |

* cited by examiner

CRIMP CONTACT, CRIMP CONTACT WITH AN ELECTRICAL LEAD, GAS SENSOR INCLUDING SAID CRIMP CONTACT AND METHOD FOR MANUFACTURING SAID GAS SENSOR

BACKGROUND OF THE INVENTION

1. Field of the Invention

The present invention relates to a crimp contact, a crimp contact with an electrical lead, a gas sensor provided with said crimp contact and a method for manufacturing said gas sensor including said crimp contact. In particular, the crimp contact includes a hold portion crimping lead core wires of an electrical lead.

2. Description of the Related Art

A conventional type of crimp contact is known to include a hold portion extending axially and holding lead core wires of an electrical lead therein (e.g., Patent Document 1). This hold portion comprises a pair of side portions for fixing the lead core wires by bending front end sides thereof toward the lead core wires of the electrical lead and a bottom portion connecting a rear end side of the pair of side portions.

This crimp contact with an electrical lead is manufactured as follows. First, a crimp contact is prepared. The crimp contact includes a U-shaped hold portion comprising a bottom portion and a pair of side portions rising from both ends of the bottom portion. Further, lead core wires of an electrical lead are disposed so as to be in contact with an inner surface of the U-shaped hold portion. Subsequently, the side portions are bent toward the bottom portion side by a pair of metal molds, i.e., an anvil and a crimper. At this time, the front end sides of the side portions of the U-shaped hold portion slide along a sliding face of the crimper and the side portions are deeply bent into a bundle of the lead core wires of the electrical lead. Then, the front end sides of the side portion are in contact with each other, and the lead core wires are held and crimped by the bottom portion and the side portions.

Incidentally, in the above-mentioned method for manufacturing the crimp contact, a crimping process of the U-shaped hold portion is conducted continuously. Consequently, slidability gradually deteriorates between the outer surfaces of the side portions and the sliding face of the crimper as the metal molds are used repeatedly in the crimping process. When the slidability deteriorates, the front end sides of the side portions insufficiently penetrate the lead core wires, and a crimping height, which is the height of the hold portion, is increased. Thereby, the lead core wires are insecurely fixed in the hold portion. As a result, electrical conductivity between the electrical lead and the crimp contact can deteriorate. In recent years, due to a demand for crimp contact durability and the like, the crimp contact tends to be made of a material having a high degree of Vickers hardness, such as INCONEL (trademark of INCO). Therefore, the slidability between the crimp contact and the crimper tends to deteriorate as the crimper is worn out. Also, the hold portion of the crimp contact tends to adhere to the crimper. Thus, as disclosed in Patent Document 1, a lubricant is applied in advance to the sliding face of the crimper so that slidability may be maintained and the hold portion with an appropriate crimping height can be formed even though the crimping process is performed continuously. As a result, the electrical conductivity between the electrical leads and the crimp contacts can be increased.

Such a crimp contact is assembled in a gas sensor having, for example, a sensor element, a metal housing and a protective cover. Here, the sensor element extends in the axial direction and includes a sensing portion in a front end side thereof. The metal housing is a cylindrical member for holding the sensor element therein so that at least the sensing portion may be exposed from a front end side of the metal housing. The front end side of the protective cover is connected to the rear end side of the metal housing, and the protective cover accommodates therein the electrical leads electrically connected to the external device. The crimp contact electrically connects the sensor element to the electrical lead and is used for outputting a signal from the sensing portion to an external device. The gas sensor is mounted on, for example, an exhaust system of an engine exhaust pipe or the like and used for detecting a gas to be measured (e.g., oxygen, nitrogen, etc.) in an exhaust gas.

[Patent Document 1] Japanese Patent Application Laid-Open (kokai) No. 64-41184

3. Problems to be Solved by the Invention

However, in Patent Document 1, a lubricant must be applied to a sliding face of a crimper at every crimping operation, which complicates the manufacturing process of the crimp contact. Further, the lubricant tends to adhere to outer surfaces of both side portions of a hold portion. This is because the lubricant is applied in advance to a sliding face of the crimper. When a gas sensor having such a crimp contact is used as an oxygen sensor mounted on, for example, an engine exhaust pipe or the like, the temperature of the hold portion of the crimp contact becomes considerably high. As a result, the lubricant, which adheres to the outer surfaces of the side portions of the hold portion, is thermally decomposed and generates a decomposition gas. Further, the thus-produced decomposition gas causes a fluctuation in the electromotive voltage of the gas sensor, thereby resulting in a measurement error. Furthermore, the specification of Patent Document 1 discloses that a lubricant (e.g., tetrafluoroethylene, carbon or the like), which does not generate a decomposition gas, is preferably selected for a crimp contact provided in an oxygen sensor or the like. However, it is troublesome to select a type of lubricant according to the environment where the gas sensor is to be used.

SUMMARY OF THE INVENTION

The present invention has been achieved in view of the above problems of the prior art, and an object of the invention is to provide a crimp contact, a crimp contact with an electrical lead, a gas sensor including the crimped contact and a method for manufacturing a gas sensor, wherein slidability between an outer surface of a hold portion and a sliding face of a crimper is secured without applying any lubricant to the sliding face of the crimper, and wherein the crimp contact can be used in a high temperature environment.

The above object of the present invention has been achieved by providing a crimp contact comprising: a terminal portion for electrical connection to another member; and a hold portion for holding lead core wires of an electrical lead therein so as to be electrically connected to said electrical lead, said hold portion including a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, and wherein a metal layer comprising Ag or Au as a main component covers at least part of an outer surface of said front end sides of said pair of side portions.

In the crimp contact having the above-described configuration, since a metal layer is formed on outer surfaces of the front end sides of the side portions, the outer surfaces of a pair of side portions may contact a sliding face of a metal mold via the metal layer when the side portions are bent by the metal mold. This metal layer includes Ag or Au as a main component (i.e., more than 50 wt %) and is capable of enhancing and maintaining slidability between the outer surface of both side portions of the hold portion and the sliding face of the metal mold when the side portions of the hold portion are bent by the metal mold. Therefore, the front end sides of a pair of side portions can sufficiently penetrate a bundle of the lead core wires. As a result, electrical conductivity is secured between the electrical lead and the crimp contact. In particular, even though the hold portion has a Vickers hardness of 350 HV or more, slidability between the outer surface of both side portions of the hold portion and the sliding face of the metal mold may be fully maintained. Since the metal layer is formed on each hold portion, gradual deterioration in slidability between the outer surface of the hold portion and the sliding face of the metal mold can be prevented, despite the continuous crimping operation. That is, slidability between the outer surface of the hold portion and the sliding face of the metal mold can be constantly maintained without applying a lubricant to the sliding face of the metal mold. Further, the metal layer is unlikely to melt under exposure to heat during the crimping operation or a high temperature environment because the metal layer has a relatively high heat resistance. The Vickers hardness of the hold portion is preferably 600 HV or less. When the Vickers hardness of the hold portion exceeds 600 HV, the hold portion is difficult to bend.

The metal layer may be formed either on the outer surfaces of the front end sides of the side portions or on the entire outer surface of the side portions. Further, the metal layer may be formed not only on the side portion but may also be formed on an outer surface of the bottom portion.

The metal layer of the crimp contact preferably has a Vickers hardness of 100 HV or less.

In the crimp contact having the above-described configuration, since the metal layer itself is soft to the extent that it has a Vickers hardness of 100 HV or less, slidability can be more efficiently secured between the hold portion and the metal mold. Therefore, when crimping the hold portion by the metal mold, slidability is further maintained between the outer surface of the hold portion and the sliding face of the metal mold. In addition, the Vickers hardness of the metal layer can be ascertained from the material hardness of the metal layer. Examples of materials having a Vickers hardness of 100 HV or less include pure Au, pure Ag or the like. However, the Vickers hardness of the metal layer is preferably 10 HV or more.

According to the crimp contact of the invention, the metal layer has a thickness of 0.1 μm or more.

In the crimp contact having the above-described configuration, due to its thickness of 0.1 μm or more, the metal layer offers secure slidability between the metal layer and the sliding face of the metal mold. Further, the metal layer is capable of protecting the metal mold from being worn out, whereby the hold portion is unlikely to adhere to the metal mold. As a result, the life of the metal mold can be extended while maintaining sufficient slidability between the metal layer and the sliding face of the metal mold. On the other hand, the thickness of the metal layer is preferably 2 μm or less. When the thickness of the metal layer exceeds 2 μm, the metal layer is more easily peeled off from the hold portion at the time of bending the side portions toward the bottom portion side by an anvil and a crimper.

According to the crimp contact of the invention, a strike plating layer including Au as a main component is formed between the metal layer and the outer surfaces of said front end sides of said pair of side portions.

In the crimp contact having the above-described configuration, a strike plating layer including Au as a main component (i.e., more than 50 wt %) is formed between the metal layer and the outer surfaces of the front end sides of the side portions so as to improve adhesion of the metal layer to the outer surface. As a result, the metal layer becomes less prone to peeling.

In the crimp contact having the above-described configuration, one of outer surfaces of the front end side of the side portion is in contact with the other outer surface of the front end side of the side portion so that the hold portion can tightly crimp the lead core wires.

According to a second aspect, the above object of the invention has been achieved by providing a crimp contact with an electrical lead comprising: an electrical lead including lead core wires and a cover member exposing said lead core wires from one end thereof, and a crimp contact including a terminal portion for electrical connection to another member and a hold portion holding said lead core wires of said electrical lead therein so as to be electrically connected to said electrical lead, said hold portion including a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, and wherein a metal layer including Ag or Au as a main component covers at least a part of an outer surface of said front end sides of said pair of side portions.

In the crimp contact having the above-described configuration, since the metal layer is formed at least on the outer surfaces of the front end sides of the side portions, the outer surfaces of the pair of side portions may be in contact with the sliding face of the metal mold via the metal layer when the side portions are bent by the metal molds. This metal layer includes Ag or Au as a main component (i.e. 50 wt % or more) and is capable of enhancing and maintaining slidability between the outer surface of both side portions of the hold portion and the sliding face of the metal mold when the side portions of the hold portion are bent by the metal molds. Therefore, the front end sides of a pair of side portions can sufficiently penetrate a bundle of the lead core wires. As a result, electrical conductivity is secured between the electrical lead and the crimp contact. In particular, even though the hold portion has a Vickers hardness of 350 HV or more, slidability between the outer surface of the hold portion and the sliding face of the metal mold may be fully maintained. Since the metal layer is formed on each hold portion, a gradual deterioration in slidability can be prevented between the outer surface of the hold portion and the sliding face of the metal mold, despite the continuous crimping operation. That is, slidability between the outer surface of the hold portion and the sliding face of the metal mold can be constantly maintained without applying any lubricant to the sliding face of the metal mold. Further, the metal layer is unlikely to melt under exposure to heat during the crimping operation or the high temperature environment because the metal layer has good heat resistance.

According to a third aspect, the above object of the invention has been achieved by providing a gas sensor, comprising: a sensor element extending in an axial direction and including a sensing portion at a front end side thereof; a cylindrical metal housing which holds said sensor element so that at least said sensing portion is exposed from a front end side of said metal housing; a protective cover including a front end connected to a rear end side of said metal housing, said protective cover accommodating therein at least one electrical lead for electrical connection to an external device; said electrical lead including lead core wires and a cover member exposing said lead core wires at one end thereof; and a crimp contact electrically connecting said sensor element to said electrical lead and adapted for outputting a signal from said sensing portion to an external device, wherein said crimp contact includes: a terminal portion for electrical connection to said sensor element and a hold portion holding said lead core wires of said electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, and wherein a metal layer including Ag or Au as a main component covers at least part of an outer surface of said front end sides of said pair of side portions.

In a gas sensor having the above-described configuration, since the metal layer formed on the crimp contact has good heat resistance, the metal layer of the crimp contact does not melt or produce a decomposition gas under exposure to a high temperature environment while using the gas sensor. As a result, the metal layer does not cause fluctuation in the electromotive voltage of the gas sensor.

Further, according to a forth aspect, the above object of the invention has been achieved by providing a method for manufacturing a gas sensor, the gas sensor comprising: a sensor element extending in an axial direction and including a sensing portion at a front end side thereof; a cylindrical metal housing which holds said sensor element so that at least said sensing portion is exposed from a front end side of said metal housing; a protective cover including a front end connected to a rear end side of said metal housing, said protective cover accommodating therein at least one electrical lead for electrical connection to an external device; an electrical lead including lead core wires and a cover member exposing said lead core wires at one end thereof; and a crimp contact electrically connecting said sensor element to said electrical lead and adapted for outputting a signal from said sensing portion to an external device, wherein said crimp contact includes: a terminal portion for electrical connection to another member; and a hold portion holding said lead core wires of said electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions, said method comprising: a plating step which comprises forming a metal layer covering at least a portion on one surface of a metal plate which is to become said front end sides of said side portions, said metal layer including Ag or Au as a main component; a press molding step which comprises pressing said metal plate so as to form a U-shaped hold portion including said pair of side portions and said bottom portion so that said one surface of said metal plate is an outer surface; and a crimping step which comprises disposing said lead core wires in said U-shaped hold portion and bending said side portions by a pair of an anvil and a crimper so that said hold portion crimps said lead core wires, and wherein said metal plate has a Vickers hardness of 350 HV or more.

In the above-described method, since a plating step is performed prior to a press molding step, the metal plating can be applied to a metal plate before press molding an U-shaped hold portion. Therefore, the metal layer can be easily formed.

In the plating step, the metal plating is preferably applied to only one side of the metal plate, which is to serve as an outer surface of the U-shaped hold portion. This is because the cost of plating can be saved as compared to the case where the metal plating is applied to both sides of the metal plate.

In the crimping step, a bundle of the lead core wires disposed within the U-like shaped hold portion is crimped by the hold portion using the anvil and the crimper. At this time, the outer surfaces of the front end sides of a pair of side portions smoothly slides along the sliding face of the crimper through the metal layer, and the front end sides of the pair of side portions can tightly dig into or rather penetrate the bundle of the lead core wires. Further, since the metal layer is formed at least on the outer surfaces serving as front end sides of the side portions of the U-shaped hold portion, the outer surfaces serving as front end sides of the pair of side portions are prevented from adhering to the sliding faces of the anvil and the crimper after the crimping step. Furthermore, the metal plating has ductility, thereby securing slidability between the outer surface of the U-shaped hold portion and each sliding face of the anvil and the crimper. As a result, the operating life of the metal mold can be extended without being damaged by consecutive crimping operations. Thus, the crimp contact having a proper crimping height can be produced consistently.

The metal plating may be applied not only to the portion serving as front end sides of the side portions of the hold portion, but also to the portion serving as entire surfaces of the side portions of the hold portion. Further, the metal plating may be applied to the portion not only serving as side portions but also serving as a bottom portion.

According to the method for manufacturing the gas sensor, the method further comprises: a strike plating step which comprises applying an Au strike plating so as to cover at least a portion on one surface of said metal plate which is to become said front end sides of said side portions, wherein said strike plating step is performed prior to said plating step.

In the above-described method, an Au strike plating is applied at least to a portion on one side of a metal plate where the front end sides of the side portions are to be formed, and the strike plating step is performed prior to said plating step. Therefore, the adhesion between the metal layer and the metal plate can be improved via the Au strike plating layer, thereby preventing the metal layer from being peeled off from the hold portion.

According to a fifth aspect, the above object of the invention has been achieved by providing a method for manufacturing a gas sensor, said gas sensor comprising: a sensor element extending in an axial direction and including a sensing portion at a front end side thereof; a cylindrical metal housing which holds said sensor element so that at least said sensing portion is exposed from a front end side of said metal housing; a protective cover including a front end connected to a rear end side of said metal housing, said protective cover accommodating therein at least one electrical lead for electrical connection to an external device; said electrical lead including lead core wires and a cover member exposing said lead core wires at one end thereof; and a crimp contact electrically connecting said sensor element to said electrical lead and adapted for outputting a signal from said sensing portion to an external device. Furthermore, said crimp contact includes: a terminal portion for electrical connection to another member; and a hold portion holding lead core wires of an electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions; said method comprising: a press molding step which comprises pressing a metal plate to form a U-shaped hold portion including said pair of side portions and said bottom portion, said metal plate having a Vickers hardness of 350 HV or more; a plating step which comprises forming a metal layer covering at least part of an outer surface of said front end sides of said side portions of said U-shaped hold portion; and a crimping step which comprises disposing said lead core wires in said U-shaped hold portion and bending said pair of side portions by a pair of an anvil and a crimper so that said hold portion crimps said lead core wires.

In the above-described method, since the plating step is performed after the press molding step, for example, an U-shaped hold portion formed in the press molding step can be immersed in a plating bath so that the metal plating may be easily formed on the outer surface of the U-shaped hold portion. Further, since the metal plating is performed after forming the U-shaped hold portion, any excess metal plating can be avoided, thereby reducing the cost of the metal plating. In the crimping step, the lead core wires are disposed so as to be in contact with an inner surface of the U-like shaped hold portion, and subsequently the thus-prepared hold portion is crimped between the anvil and the crimper. At this time, the outer surfaces of the front end sides of a pair of side portions smoothly slide along the sliding face of the crimper via the metal layer, and the front end sides of the pair of side portions can tightly dig into or rather penetrate the lead core wires. Further, since the metal layer is formed on the outer surface of the U-shaped hold portion, the outer surfaces of the front end sides of the pair of side portions are prevented from adhering to the sliding faces of the anvil and the crimper after the crimping step. Furthermore, the metal plating has ductility, thereby securing slidability between the outer surface of the U-shaped hold portion and each sliding face of the anvil and the crimper. As a result, the crimping operation of a plurality of U-shaped hold portions can be preformed consecutively, and the crimp contact provided with the hold portion constantly having a proper crimping height can be formed consistently.

According to the fifth aspect of the invention, the method may further comprise: a strike plating step which comprises applying an Au strike plating so as to cover at least a portion on one surface of said metal plate which to become said front end sides of said side portions, wherein said strike plating step is performed between said press molding step and said plating step.

In the method having the above mentioned process, an Au strike plating is applied at least to a portion on one side of a metal plate where the front end sides of the side portions are to be formed, and the strike plating step is performed prior to said plating step. Therefore, due to the strike plating layer, adhesion between the metal layer and the metal plate can be improved, thereby protecting the metal layer from being peeled off from the hold portion.

DESCRIPTION OF REFERENCE NUMERALS

Figure 1:
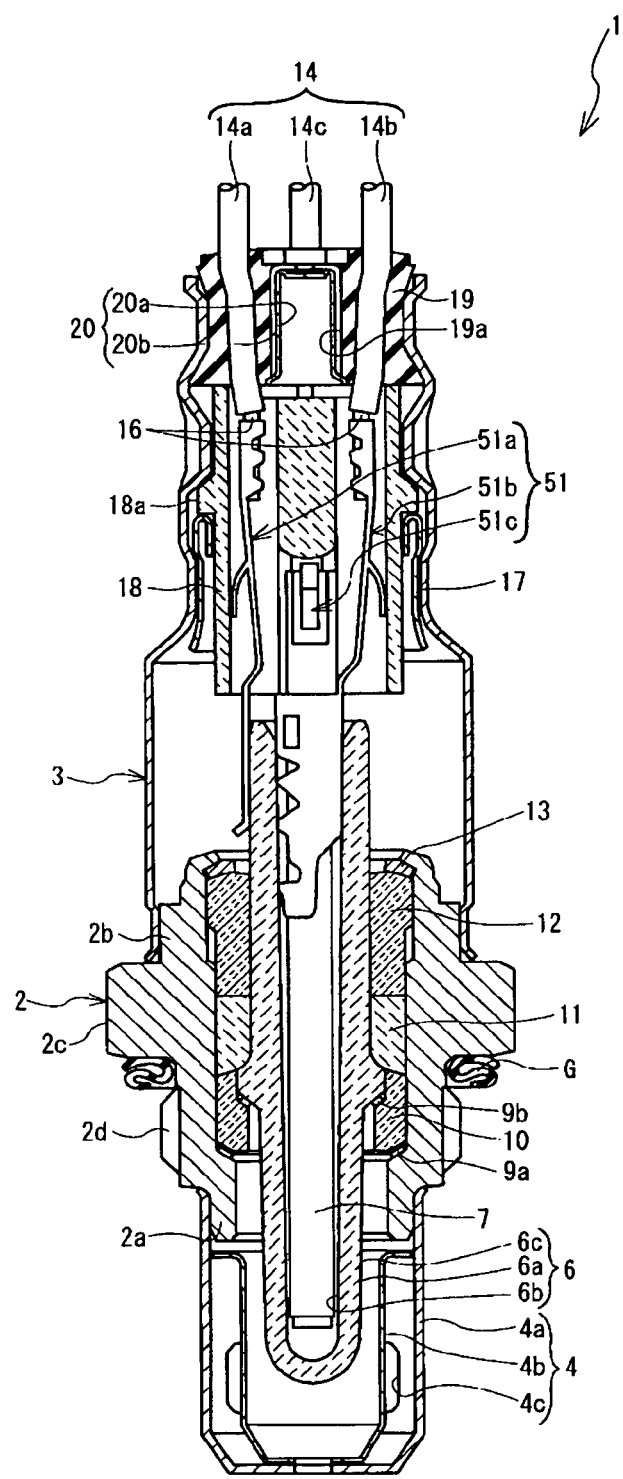
FIG. 1 is a sectional view of a gas sensor 1 according to an embodiment of the present invention.

Reference numerals used to identify various structural features shown in the drawings including the following.

1 gas sensor; 2 metal shell; 3 protective cover; 6 sensor element; 14 electrical lead; 16 lead core wire; 51b crimp contact; 57 hold portion; 57a bottom portion; 57b side portion; 57c front end side; 67 flat hold portion; 77 U-shaped hold Portion; 77a bottom portion; 77b side portion; 77c front end side; 80 metal plate; 85 plating layer; 120 anvil; 121 crimper.

DETAILED DESCRIPTION OF THE PREFERRED EMBODIMENTS

Hereafter, a gas sensor 1 according to an embodiment of the present invention will be explained with reference to the drawings. However, the present invention should not be construed as being limited thereto.

FIG. 1 is a sectional view of a gas sensor 1 according to an embodiment of the present invention. As used herein, the term "front end side" refers to a lower side of the gas sensor 1 in FIG. 1 and the term "rear end side" refers to an upper side of the gas sensor 1 in FIG. 1.

The gas sensor 1 is adapted for use in an automotive exhaust pipe as an oxygen sensor to detect oxygen concentration in exhaust gas flowing through the exhaust pipe.

First, the gas sensor 1 will be described. As shown in FIG. 1, the gas sensor 1 is mainly comprised of: a generally cylindrical metal shell 2; a sensor element 6 detecting the concentration of a specific gas (e.g., oxygen) in an exhaust gas; a ceramic heater 7 for heating the sensor element 6; a protector 4 protecting a front end side of the sensor element 6; a separator 18 made of alumina and accommodating therein four crimp contacts 51 (only three of the crimp contacts are illustrated in FIG. 1) fixed to four electrical leads 14 (only three of the electrical leads are illustrated in FIG. 1), respectively; and a generally cylindrical protective cover 3 enclosing the separator 18 to protect the same. The sensor element 6 and the ceramic heater 7 extend in an axial direction of the gas sensor 1. In addition, the metal shell 2 shown in FIG. 1 serves as a "metal housing".

First, the sensor element 6 is comprised of: a solid electrolyte element 6a; an inner electrode 6b formed on an inner surface of the solid electrolyte element 6a with Pt or a Pt alloy; and an outer electrode 6c formed on an outer surface of the solid electrolyte element 6a.

The metal shell 2 is formed so as to accommodate the sensor element 6 therein. A rear end side of the metal shell 2 is radially inwardly crimped, and a sensing portion formed at a front end side of the sensor element 6 is exposed from the front end side of the metal shell 2 so as to be held in an insulated manner. Further, the metal shell 2 has a cylindrical boss portion 2b at the rear end side thereof. Furthermore, the front end side of the metal protective cover 3 is fixed to the boss portion 2b.

On the other hand, the metal shell 2 has a cylindrical boss portion 2a at the front end side thereof, and the metal protector 4 is connected to the boss portion 2a. The protector 4 is comprised of an outer protector 4a located at the outer side and an inner protector 4b fixed in the outer protector 4a, wherein the rear end side of the outer protector 4a is fixed to the outer circumference of the boss portion 2a. Further, gas holes 4c are formed in the protector 4 so that the gas whose oxygen concentration is measured may flow to the sensing portion of the sensor element 6 through the gas holes 4c (the gas holes in the inner protector 4b are not shown).

The sensor element 6 is inserted in the metal shell 2 through a metal packing 9a, a ceramic holder 10, a metal packing 9b, a sealing powder material 11 made of talc or the like, a ceramic sleeve 12 and a metal ring 13. Further, the ceramic heater 7 is inserted in the sensor element 6 from the rear end side to the front end side. Furthermore, a flange 2c projecting radially outwardly is provided on an outer surface of the rear end side of the metal shell 2. A male screw thread 2d for fixing the metal shell 2 to an exhaust pipe (not illustrated) is formed between the flange 2c and the boss portion 2a. Moreover, a gasket G is fixed between the male screw 2d and the flange 2c.

On the other hand, a separator 18 is inserted in the protective cover 3. A flange 18a projecting radially outwardly is formed on an outer circumference of the separator 18, and a generally cylindrical separator holder 17 is placed between the protective cover 3 and the separator 18 at the further front end side from the flange 18a. That is, while the separator holder 17 holds and accommodates the separator 18 therein, the separator holder 17 is enclosed by the protective cover 3. Further, inside the separator 18, four crimp contacts 51 are electrically connected to the front end side of a plurality of lead core wires 16 accommodated in each electrical lead 14, respectively.

In detail, each electrical lead 14 is comprised of electrical leads for an element 14a, 14b and electrical leads for a heater 14c, 14d (not illustrated). The lead core wire 16 of the electrical lead for an element 14a is mechanically connected to a crimp contact 51a fitted to the outer surface of the sensor element 6, and the electrical lead for an element 14a is electrically connected to the outer electrode 6c of the sensor element 6. Further, the lead core wire 16 of the electrical lead for an element 14b is mechanically connected to a crimp contact 51b press fitted to the inner face of the sensor element 6, and the electrical lead for an element 14b is electrically connected to the inner electrode 6b of the sensor element 6. The lead core wires 16 of the electrical leads for a heater 14c, 14d are respectively connected to a pair of crimp contacts 51c joined to a heat generating resistor of the ceramic heater 7.

Further, a grommet 19 made of rubber is inserted into the rear end side of the protective cover 3 adjacent to the separator 18. Then, four electrical leads 14 extend to the outside from the gas sensor 1 through the grommet 19. Furthermore, a through-hole 19a is formed in the center of the grommet 19, and a filter unit 20 is fitted in the through-hole 19a. The filter unit 20 is comprised of a metal cylindrical filter holder 20a and a filter 20b made of PTFE and covered by a circumferential face and an upper surface of the filter holder 20a (rear end side of the gas sensor 1). Thus, atmospheric air at the rear end side of the gas sensor 1 may communicate to the inside of the protective cover 3 through the through-hole 19a and the filter 20b of the filter unit 20.

Figure 2:
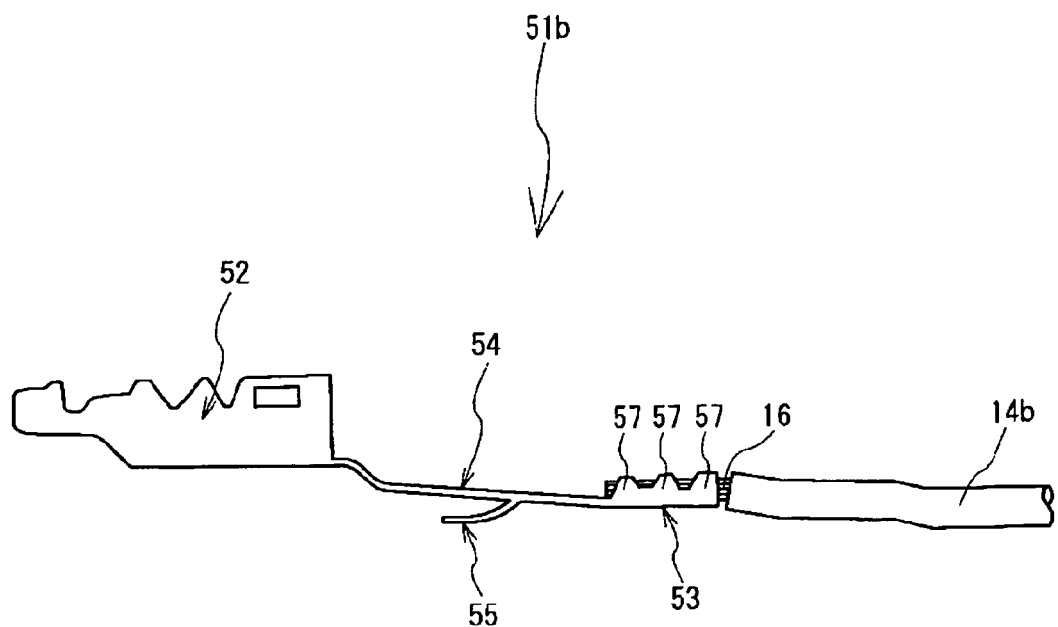
FIG. 2 is a side view showing a crimp contact 51b.

Next, the crimp contact 51b will be explained. Although the crimp contact 51a, the crimp contact 51b and the crimp contact 51c each has a different shape, only the crimp contact 51b will be described. The detailed explanation regarding the crimp contact 51a and the crimp contact 51c will be omitted below because the hold portion of the crimp contact 51b, which is a principal part of the present invention, is the same as the hold portion in the other crimp contacts. As shown in FIG. 2, the entire crimp contact 51b extends parallel to the axial direction of the gas sensor 1 (refer to FIG. 1) and comprises: an element fitting portion 52 which fits into the rear end side of the sensor element 6 (refer to FIG. 1) so as to be electrically connected to the inner electrode 6b; a barrel portion 53 holding therein a plurality of lead core wires 16 of the electrical lead for an element 14b and crimped so as to be electrically connected to the electrical lead; a lead portion 54 interposed between the element fitting portion 52 and the barrel portion 53; and a retention piece 55 formed on the outer surface of the lead portion 54 in contact with an inner surface of the separator 18 (refer to FIG. 1) so as to elastically hold the crimp contact 51b.

Figure 3:
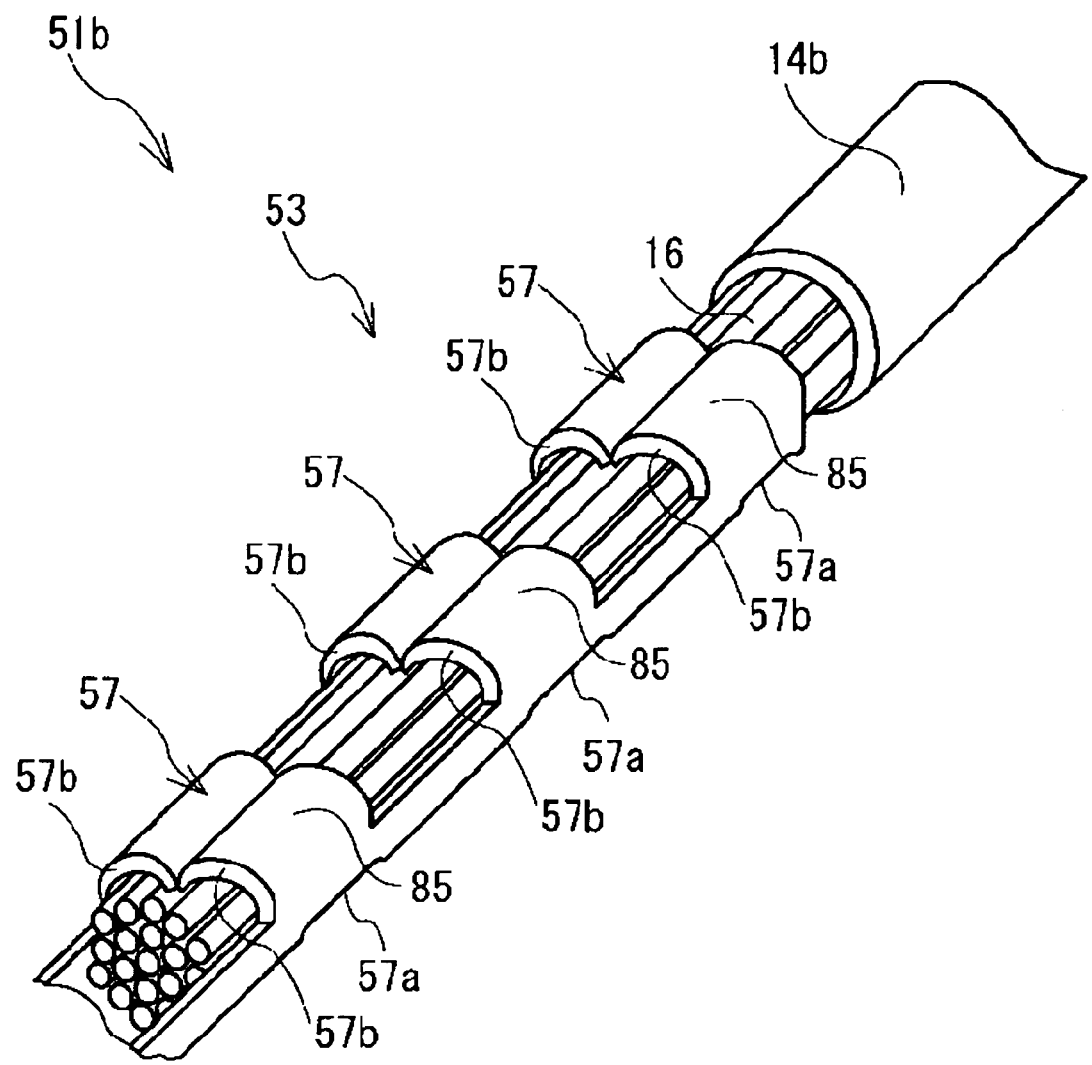
FIG. 3 is a perspective view showing a barrel portion 53.

Next, the barrel portion 53 will be described. As shown in FIG. 3, the barrel portion 53 comprises three hold portions 57. The hold portions 57 are disposed along the longitudinal direction of the barrel portion 53 with a predetermined gap therebetween. Thus, the lead core wires 16 of the electrical lead for an element 14b are placed in and enclosed by three hold portions 57 so as to be electrically connected to the barrel portion 53 of the crimp contact 51b. Further, a plating layer 85 made of Ag plating is formed on the entire outer surface of the barrel portion 53. The plating layer 85 is an aspect of the present invention and its effect will be described below.

Figure 4:
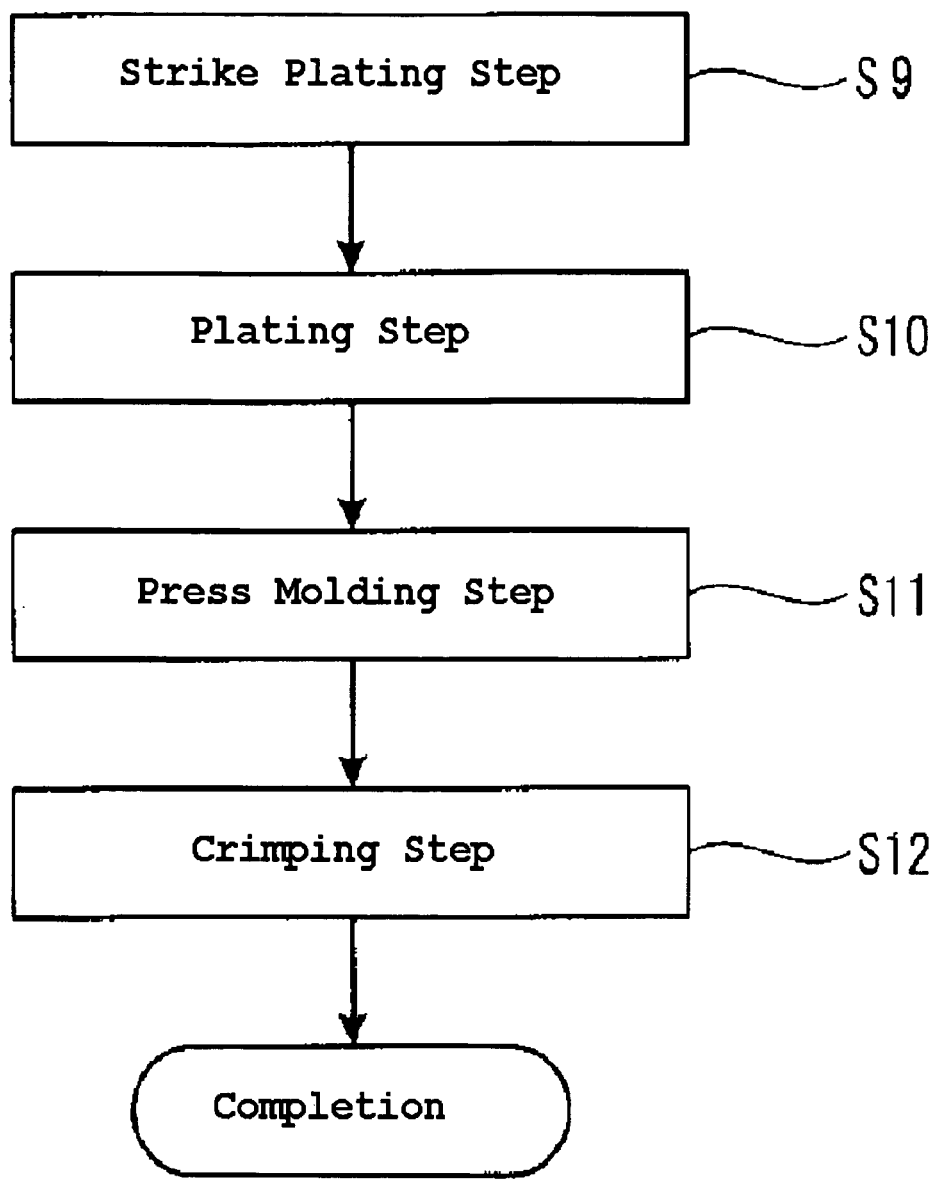
FIG. 4 is a flowchart showing steps in manufacturing a crimp contact 51b.

Next, a method for manufacturing the crimp contact 51b will be described. As shown in FIG. 4, first, a plating step (S10) that applies Ag plating to a predetermined portion on one side of a metal plate 80 (refer to FIG. 5) used as a base material of the crimp contact 51b is performed. Next, a press molding step (S11) is performed where the thus-formed Ag plated metal plate 80 in the plating step is press molded into a crimp contact 71b which includes a U-shaped hold portion 77. Finally, a crimping step (S12) is performed such that the lead core wires 16 of the electrical lead for an element 14b are disposed so as to be in contact with the inner surface of the U-shaped hold portion 77 of thus-press molded crimp contact 71b. Then the hold portion 57 is crimped onto the lead core wires 16 using a pair of metal molds—an anvil 120 and a crimper 121 (refer to FIG. 8)—to form the crimp contact 51b with the hold portion 57. The above-mentioned manufacturing steps (S9, S10, S11, S12) of the crimp contact 51b will be described in detail as follows.

Figure 5:
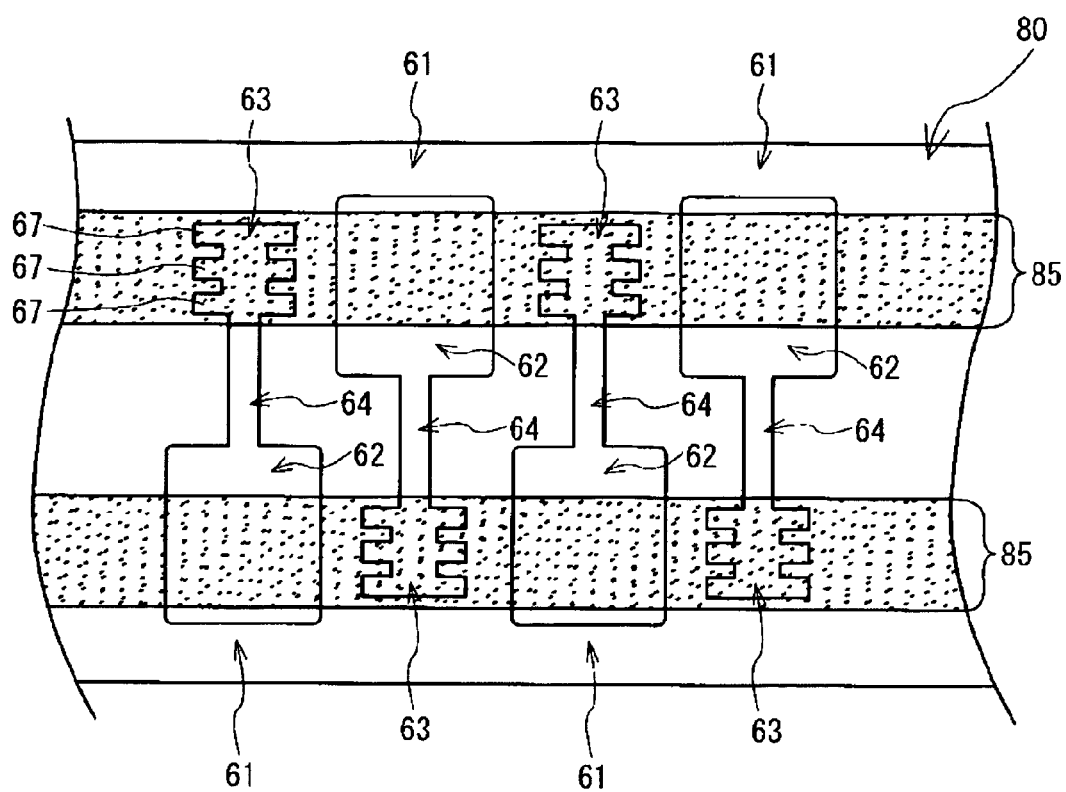
FIG. 5 is a top view showing a metal plate 80 to which a strike plating treatment is applied.

First, as shown in FIG. 5, the metal plate 80 used as a material of the crimp contact 51b is prepared. The metal plate 80 is formed in a belt-like shape and is made of INCONEL (trademark of INCO). Next, a press-mold layout of a flat terminal 61, which serves as a crimp contact 71*b* (described below), is performed to one side of the metal plate 80. The flat terminal 61 is comprised of a flat fitting portion 62, a flat barrel portion 63 and a flat lead portion 64. The flat barrel portion 63 is comprised of three pieces of flat hold portions 67. Then, a plurality of such flat terminals 61 is disposed toward the longitudinal direction of the metal plate 80. At this time, the adjacent flat terminals 61 are disposed in the reverse direction. That is, the flat barrel portions 63 of the adjacent flat terminals 61 are alternately disposed. This is for reducing residual portions of the metal plate 80 after the press molding step. In addition, the flat hold portion 67 shown in FIG. 5 is equivalent to "a portion serving as a hold portion" within the scope of the present invention.

Next, a strike plating step (S9) is performed. A masking process is performed to the other side of the metal plate 80 (the reverse side in FIG. 5) where one side thereof is subjected to the press-mold layout of the flat terminal 61. An Au strike plating is applied to the reverse side of the metal plate 80. The Au strike plating process is used for improving adhesion between an Ag plating (subsequently performed) and the INCONEL which is a base material of the metal plate 80. The strike plating is applied in a stripe shape so that the Au plating may be applied at least to the flat barrel portion 63 (three pieces of the flat hold portions 67) in each flat terminal 61 in which the press-mold layout is performed.

Then, the plating step (S10) is performed. In detail, Ag plating is applied to one side of the metal plate 80 where Au strike plating has already been applied. The plating step is performed in a manner similar to the strike plating step in which Ag plating is applied in a stripe shape and formed on the Au strike plating.

In this way, one side of the metal plate 80 has two stripes of the plating layers 85 in a plane view which are formed on the flat barrel portion 63 of the flat terminal 61. The thickness of the plating layer 85 is adjusted to 0.1 μm or more (1.0 μm in this embodiment) to thereby effectively secure slidability between the plating layer 85 formed on the outer surface of the U-shaped hold portion 77 and a sliding face of a concave portion 121*a* of the crimper 121 (refer to FIGS. 8 and 9) described below. In addition, although pure Ag plating is used as a material of the plating layer 85 in this embodiment, any metal plating having ductility and heat resistance, such as pure Au plating, may also be employed. When pure Au plating is employed, the adhesion with the Au strike plating is stronger than with the pure Ag plating. Since the plating layer 85 is formed by the metal plating with heat resistance, the plating is neither unlikely to melt nor produce any decomposition gas when the crimp contact 51*b* is employed in the gas sensor 1 mounted on an exhaust pipe of an automobile or the like and is exposed to a high temperature environment. As a result, fluctuation of the electromotive voltage of the gas sensor 1 can be prevented.

Figure 6:
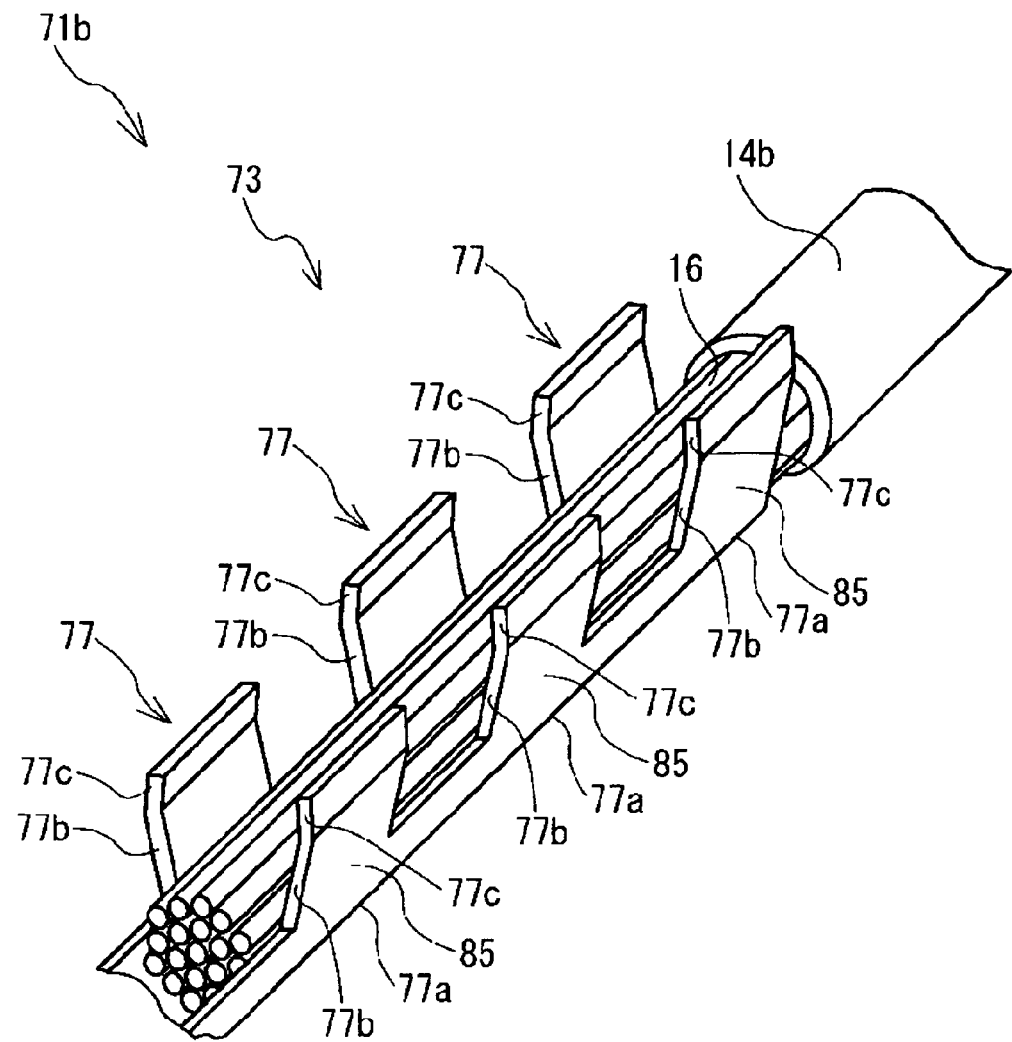
FIG. 6 is a perspective view showing the state where lead core wires 16 of an electrical lead 14b for an element is disposed in an U-shaped hold portion 77.
Figure 7:
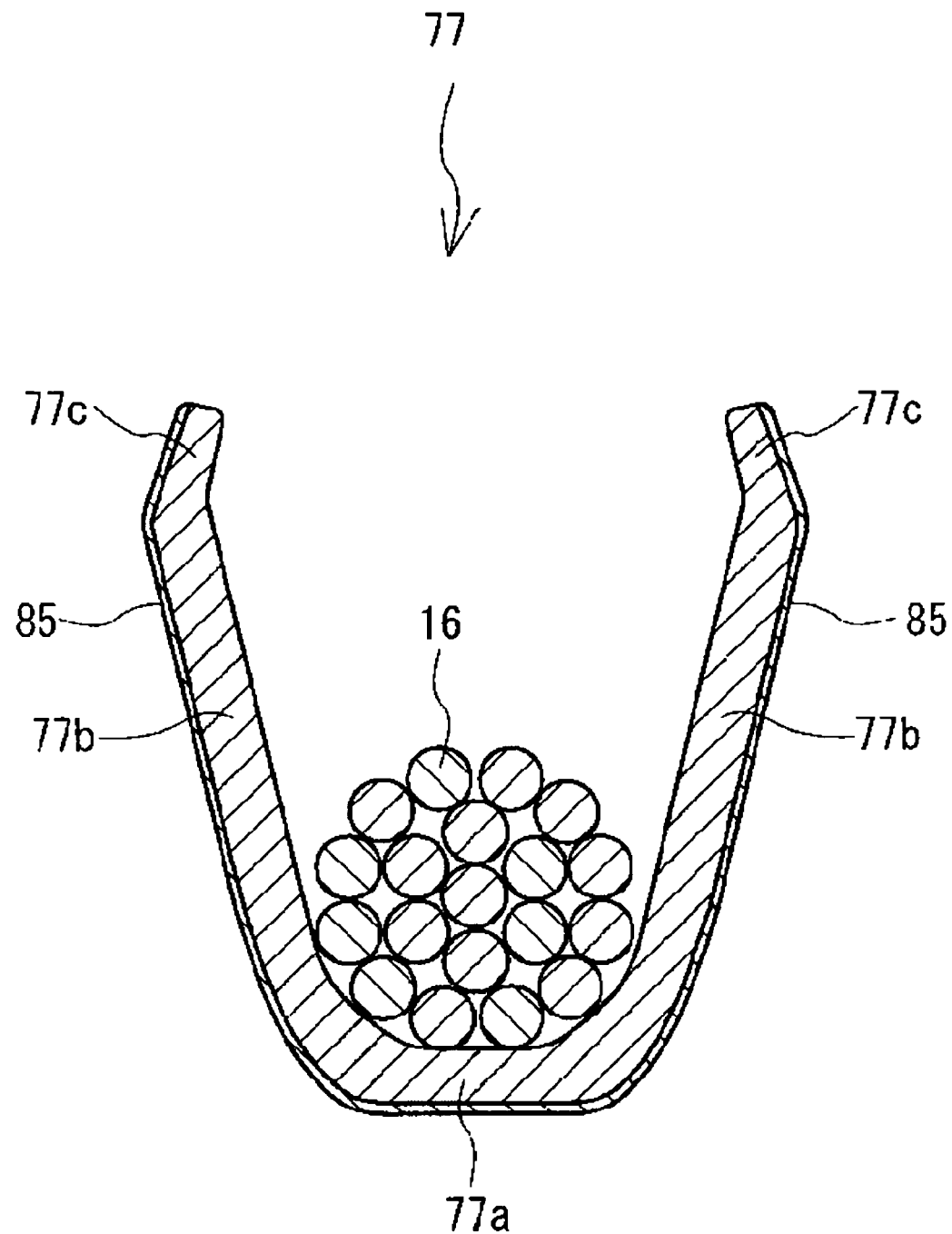
FIG. 7 is a sectional view showing an U-shaped hold portion 77.

Next, the press molding step (S11) will be described. In this press molding step, the metal plate 80 subjected to the plating step (S10) is press molded by a press machine (not illustrated). In detail, the flat terminal 61 is press molded according to the press-mold layout formed on the metal plate 80. In the flat terminal 61, the flat barrel portion 63 is press molded into an U-shape so that the plated-side on which the plating layer 85 is formed may face the outside. In this way, as shown in FIG. 6, the crimp contact 71*b* having an U-shaped barrel portion 73 is formed. Each U-shaped hold portion 77 constituting the U-shaped barrel portion 73 is formed in an U-shape, when viewed in cross section perpendicular to the axial direction, by a bottom portion 77*a* and a pair of side portions 77*b* rising from opposite ends of the bottom portion 77*a* as shown in FIGS. 6 and 7. Further, both front end sides 77*c* of the side portions 77*b*, which are located at the opposite side to the bottom portion 77*a*, incline towards each other. Furthermore, the front end sides 77*c* have a slightly thinner thickness than that of other portions of the side portions 77*b*. Moreover, the plating layer 85 is formed on the outer surface of the U-shaped hold portion 77.

Figure 8:
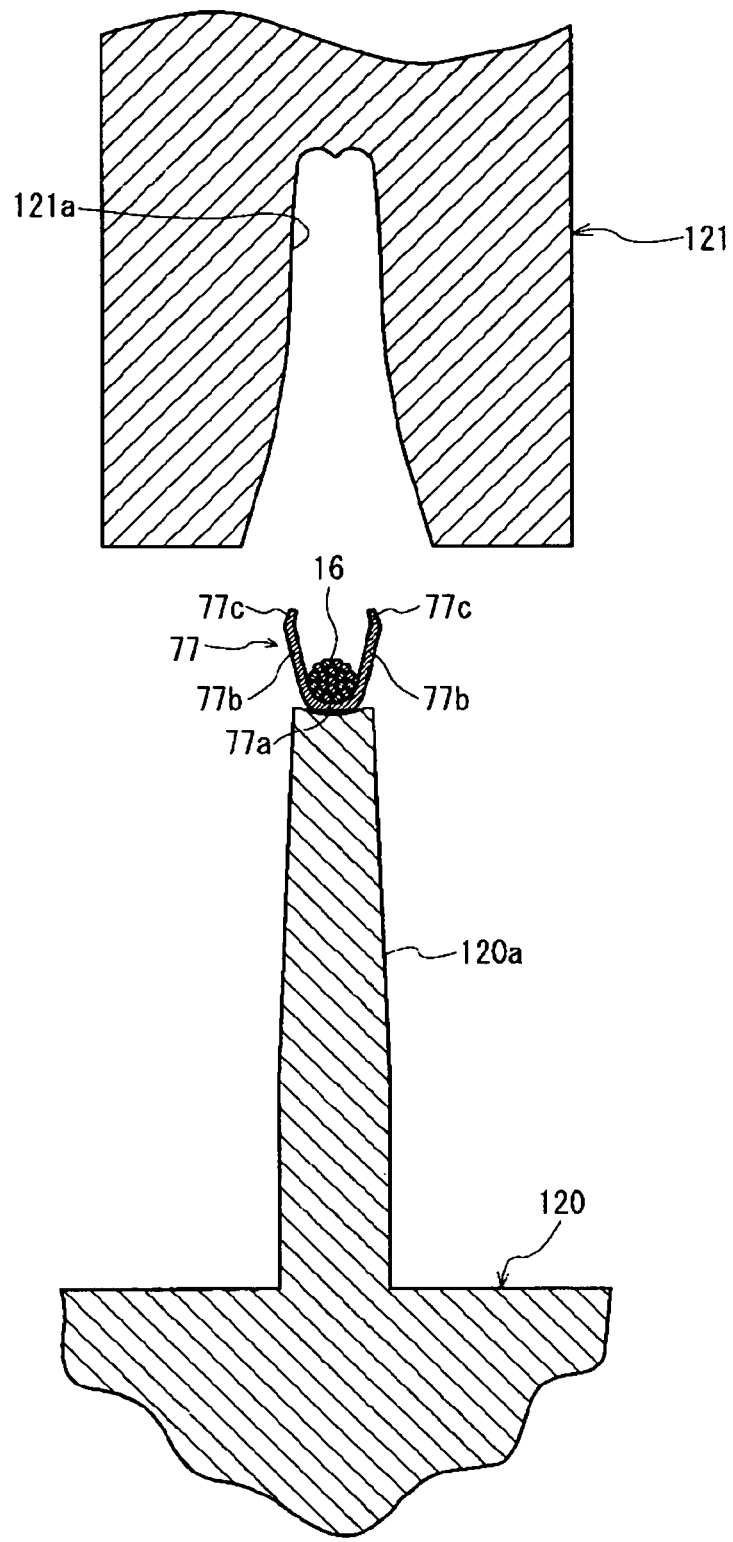
FIG. 8 is a sectional view showing the state where an U-shaped hold portion 77, is disposed between an anvil 120 and a crimper 121.

Next, the crimping step (S12) will be described. As shown in FIG. 8, a pair of metal molds—the anvil 120 and the crimper 121 are employed. The anvil 120 has a convex portion 120*a* projecting upward. On the other hand, the crimper 121 has a concave portion 121*a* opening downward. A sliding face located at the bottom of the concave portion 121*a* is formed in a generally M-shape curving from the center to both sides of the concave portion 121*a*. Further, the concave portion 121*a* and the convex portion 120*a* fit together. In such a pair of metal molds, the crimper 121 moves down towards the anvil 120 so as to crimp an object (the U-shaped hold portion 77 in this embodiment) sandwiched between the convex portion 120*a* and the concave portion 121*a*.

First, the U-shaped hold portion 77 is positioned on the upper portion of the convex portion 120*a*. At this time, the opening side of the U-shaped hold portion 77 is positioned so as to face the concave portion 121*a* of the crimper 121. Subsequently, the lead core wires 16 of the electrical lead for an element 14*b* are disposed so as to be in contact with the inner circumference face of the U-shaped hold portion 77 (refer to FIGS. 7 and 8). Thus, the lead core wires 16 are enclosed by the bottom portion 77*a* and the side portions 77*b*.

Next, the crimper 121 is moved down to the anvil 120. As mentioned above, since the front end sides 77*c* of the U-shaped hold portion 77 incline towards each other, the sliding face of the concave portion 121*a* of the crimper 121 is first in contact with the outer surface of the front end sides 77*c*. Then, the front end sides 77*c* slide along the sliding face of the concave portion 121*a* of the crimper 121 because the thickness of the front end sides 77*c* is thinner than that of other portions of the side portions 77*b*. Since the sliding face of the concave portion 121*a* of the crimper 121 is formed in a generally M-shape, which curves toward the center from both sides of the concave portion 121*a*, the front end sides 77*c* are gradually guided to incline towards each other.

Figure 9:
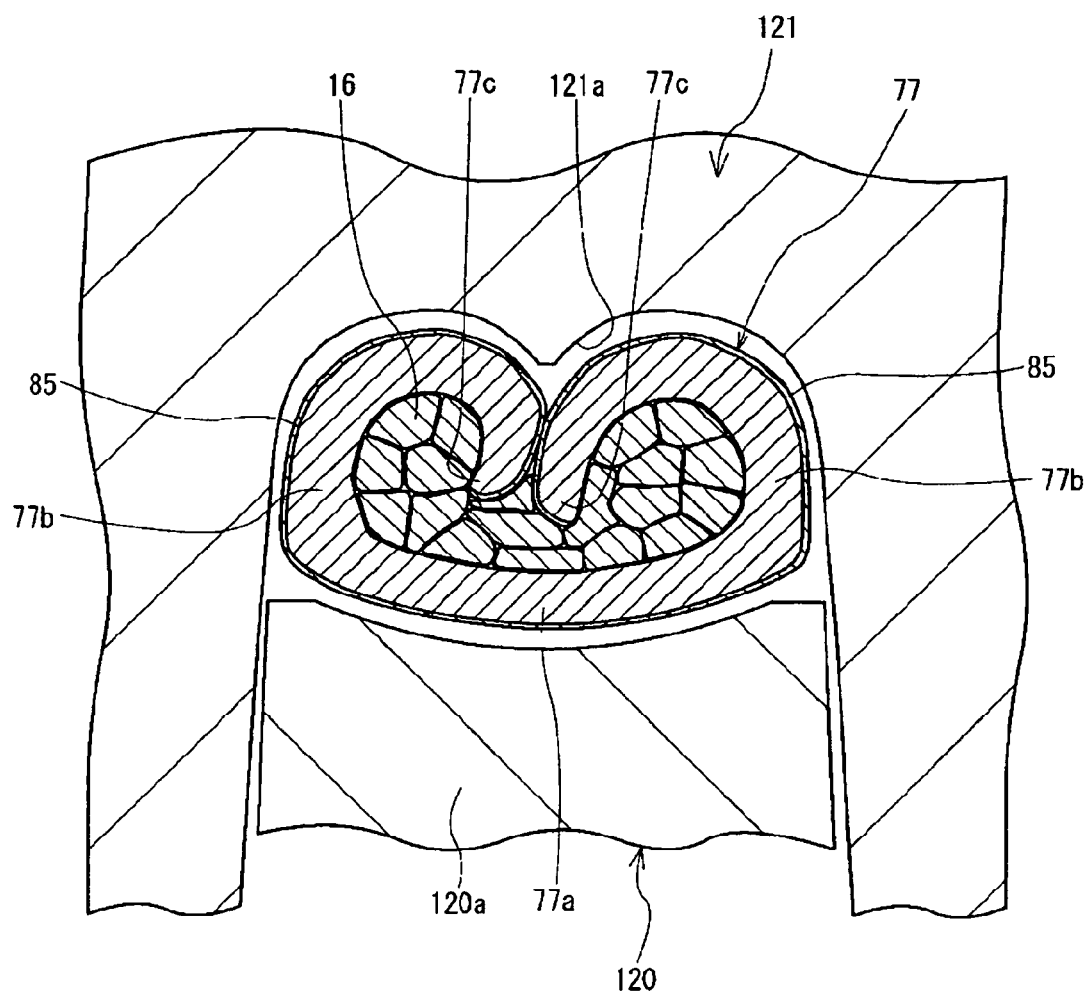
FIG. 9 is a sectional view showing the state where an U-shaped hold portion 77 is crimped between an anvil 120 and a crimper 121.

Since the plating layer 85 is formed on the outer surface of the U-shaped hold portion 77, slidability is secured between the sliding face of the concave portion 121*a* of the crimper 121 and the outer surface of the U-shaped hold portion 77. Therefore, the front end sides 77*c* are deeply bent toward the bottom portion 77*a* side like an arc, and the lead core wires 16 are tightly crimped by the bottom portion 77*a* and the side portions 77*b* as shown in FIG. 9. Further, since the sliding face of the concave portion 121*a* of the crimper 121 secures slidability along the outer surface of the U-shaped hold portion 77, the outer surface of the U-shaped hold portion 77 does not adhere to each sliding face of the anvil 120 and the crimper 121. Thereby, the hold portion 57 can be easily removed from each sliding face, and the crimp contact 51*b* is unlikely to be deformed. In this way, as shown in FIG. 10, the hold portion 57 including a plurality of lead core wires 16 is then completed.

Figure 10:
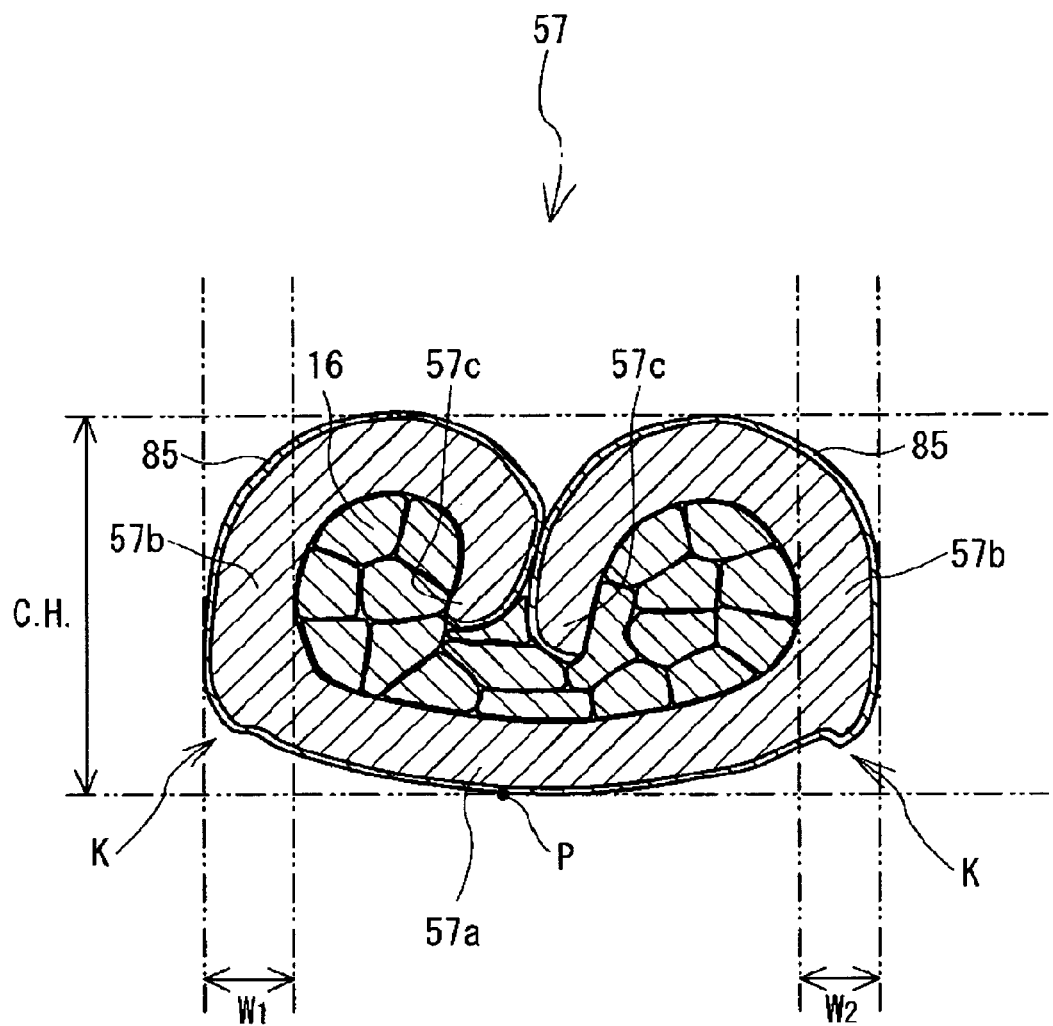
FIG. 10 is a sectional view of a hold portion 57.

As shown in FIG. 10, the hold portion 57 comprises a bottom portion 57*a* and a pair of side portions 57*b* rising from both ends of the bottom portion 57*a*, when viewed in a cross section perpendicular to the axial direction. Further, the front end sides 57*c* of the side portions 57*b* located opposed to the bottom portion 57*a* thereof are deeply bent toward the bottom portion 57*a* side. Furthermore, one of the outer surfaces of the front end side 57*c* is in contact with the other outer surface of the front end side 57c. In this way, the lead core wires 16 of the electrical lead for an element 14b are enclosed by the hold portion 57 of the crimp contact 51b and crimped by the bottom portion 57a and the side portions 57b.

The Vickers hardness of the hold portion 57 is more than 350 (HV). The Vickers hardness of the hold portion 57 is measured at plural locations in the bottom portion 57a thereof, and the average value of the measurements is adopted. The measurement conditions of Vickers hardness are: loading; 300 gf and loading time; 10 seconds.

As described above, in this embodiment, the plating layer 85 provided on the outer surface of the U-shaped hold portion 77 contributes to secure slidability between the sliding face of the concave portion 121a of the crimper 121 and the outer surface of the U-shaped hold portion 77. For example, when a plurality of U-shaped hold portions 77 is crimped consecutively, secure slidability is maintained between the outer surface of the U-shaped hold portion 77 and the sliding face of the concave portion 121a of the crimper 121. As a result, the crimp contact 51b having no failure in terms of its performance and appearance can be produced.

Next, in order to confirm the effect of the slidability provided by the plating layer 85, a consecutive crimping evaluation test using the anvil 120 and the crimper 121 was conducted on the U-shaped hold portion 77. First, in this evaluation test, a method for evaluating a hold portion 57 formed in the crimping step will be described. As shown in FIG. 10, the lowermost bottom portion of the hold portion 57 was taken as a point P. The distance (height of the hold portion 57) from the point P to the topmost portion of the hold portion 57 was taken as a C.H. (crimp height). Further, the thickness of the rising part of both side portions 57b of the hold portion 57 was taken as W1 and W2, respectively. The outer surface where the bottom portion 57a and the side portions 57b were connected was taken as point K. Then, the thus-determined reference points were used as evaluation points, and evaluations of the hold portion 57 and the crimp contact 51b were conducted considering thoroughly the following points. 1: Variation of C.H., 2: Width of W1 and W2, 3: Shape of Point K, 4: Appearance of the crimp contact 51b, etc.

First, a test 1 will be explained. In test 1, a plurality of conventional crimp contacts having no plating layer on the outer surface of an U-shaped hold portion was prepared to conduct a consecutive crimping test on U-shaped hold portions. Each C.H. (mm) of crimped hold portions was measured each time the crimping was conducted. Further, a variation of the C.H. from a default value (0 mm) of the C.H. of the hold portion, which was measured at the first crimping, was converted to variation Δh. No lubricant was employed in this evaluation.

Figure 11:
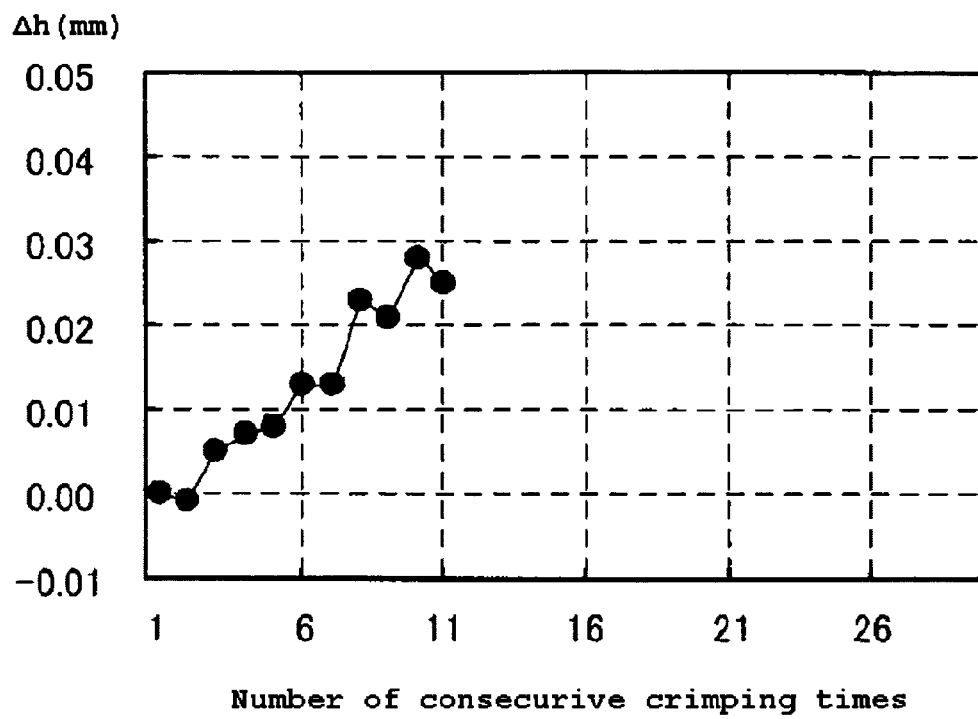
FIG. 11 is a graph showing the results of Test 1.
Figure 12:
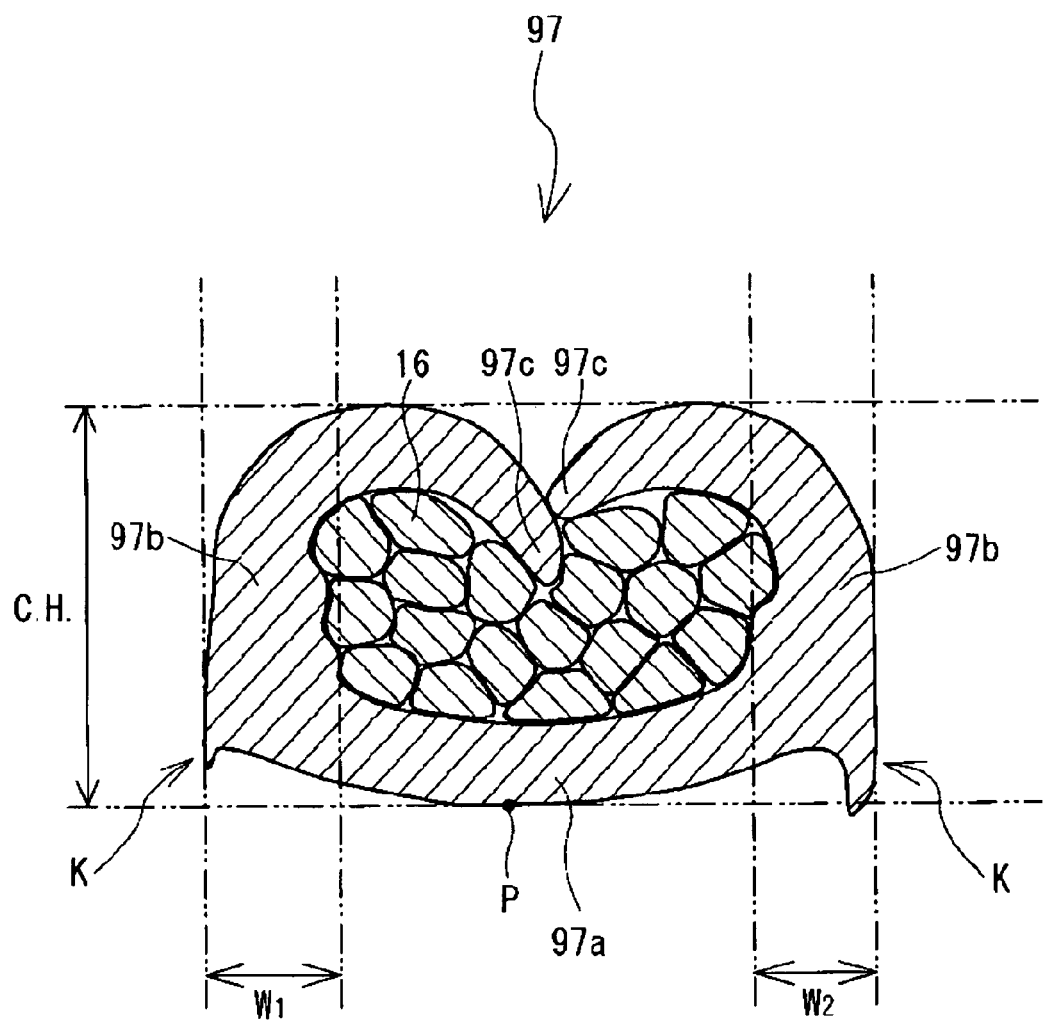
FIG. 12 is a sectional view of a hold portion 97 produced after conducting eleven consecutive crimpings.

Next, the result of test 1 will be explained. As shown in FIG. 11, after conducting three consecutive crimpings, the result was Δh=0.005 mm; after conducting six consecutive crimpings, the result was Δh=0.013 mm; after conducting nine consecutive crimpings, the result was Δh=0.021 mm; and after conducting eleven consecutive crimpings, the result was Δh=0.025 mm. According to these results, it was apparent that the greater the number of crimping times, the greater the Δh value. As shown in FIG. 12, when observing a hold portion 97 formed after conducting eleven consecutive crimpings, the C.H. of the hold portion 97 is slightly higher than that of the hold portion 57 according to the embodiment shown in FIG. 10. Further, some gaps were observed between the lead core wires 16 enclosed by a bottom portion 97a and both side portions 97b of the hold portion 97. Furthermore, the thickness of W1 and W2 increased. Also, burrs projecting downward were observed at the point K of each hold portion 97.

Next, the result of test 1 was examined. Since the slidability between the sliding face of the concave portion 121a of the crimper 121 and the outer surface of the U-shaped hold portion gradually deteriorates as the number of crimping operations increases, the front end sides of the side portions of the U-shaped hold portion did not dig into or rather penetrate the plurality of lead core wires 16. Thus, it was apparent that the height of the crimped hold portion was slightly high. Further, as shown in FIG. 12, the front end sides 97c of the side portions 97b insufficiently penetrated the plurality of lead core wires 16 and loosened, thereby resulting in failing to tightly fix the lead core wires 16. Further, the possible reason for an increase in the thickness of W1 and W2 was that the side portions 97b were pressed by the crimper 121 from the direction perpendicular to the thickness of the side portions 97b. This is because the front end portions 97c insufficiently penetrated the lead core wires 16. Furthermore, the possible reason for the burr occurring at each point K was that the side portions 97b were pressed from the direction perpendicular to the thickness of the side portions 97b, whereby a part of the side portions 97b extended downward to the gap between the anvil 120 and the crimper 121.

Next, a test 2 will be explained. In test 2, similarly to the test 1, a plurality of crimp contacts 71b according to the embodiment, in which an Ag plating layer was applied to the outer surface thereof, was prepared to conduct a consecutive crimping test on the U-shaped hold portions 77. The C.H. (mm) of crimped hold portion was measured each time a crimping operation was conducted. A variation of the C.H. from a default value (0 mm) of the C.H. of the hold portion, which was measured at the first crimping, was converted to variation Δh. No lubricant was employed in this evaluation.

Figure 13:
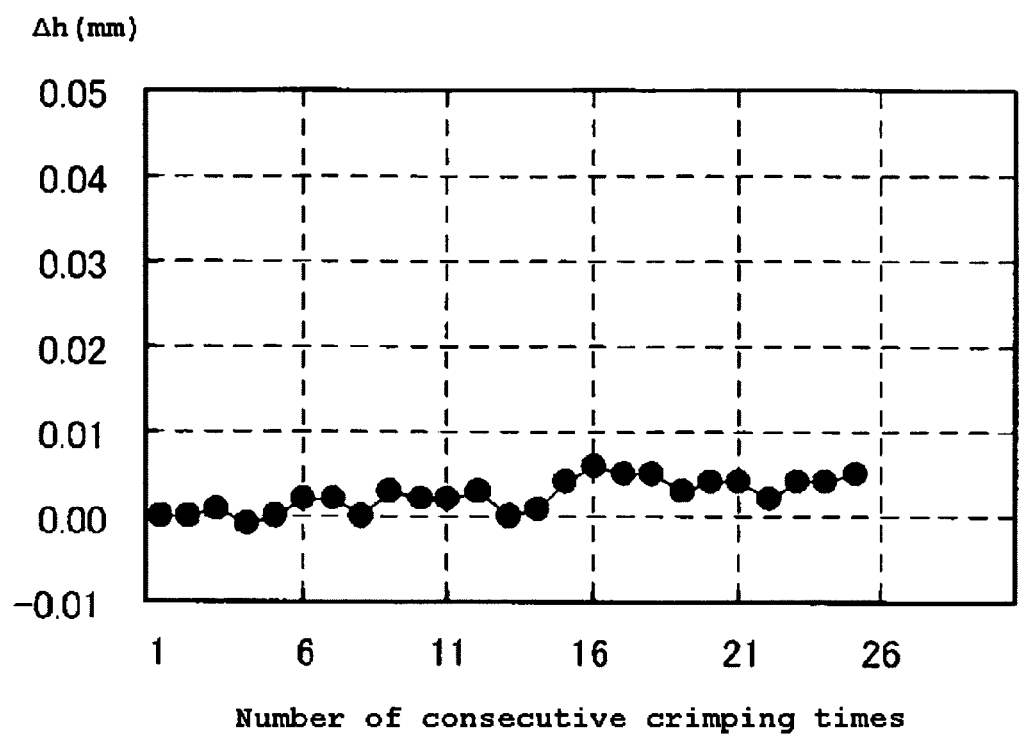
FIG. 13 is a graph showing the results of Test 2.
Figure 14:
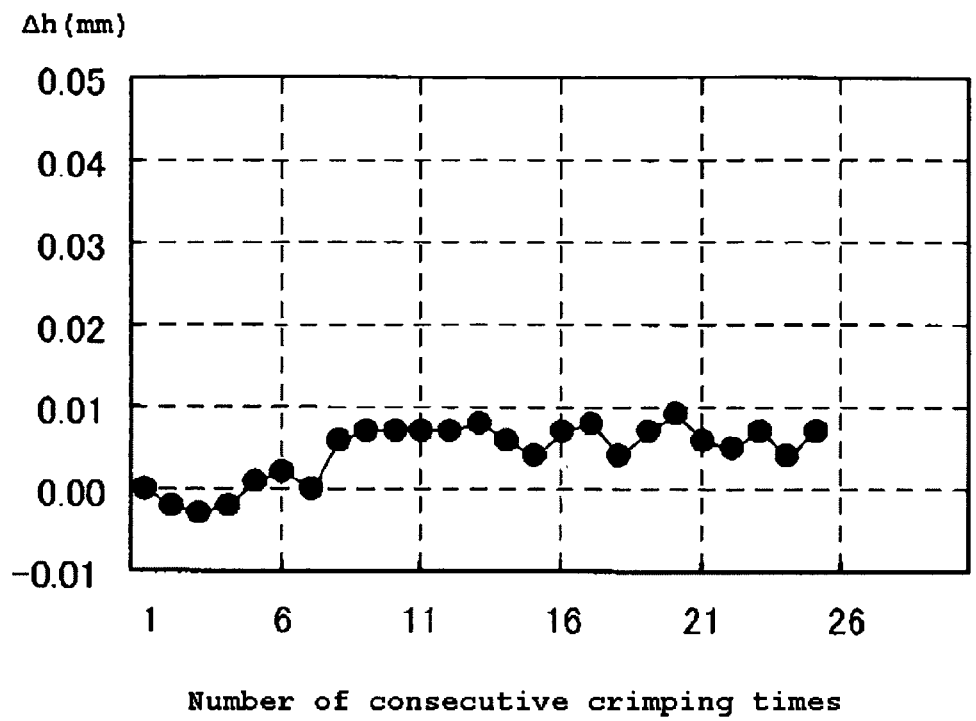
FIG. 14 is a graph showing the results of Test 3.

Next, the result of test 2 is explained. As shown in FIG. 13, after conducting three consecutive crimpings, the result was Δh=0.001 mm; after conducting six consecutive crimpings, the result was Δh=0.002 mm; after conducting eleven consecutive crimpings, the result was Δh=0.002 mm; after conducting fifteen consecutive crimpings, the result was Δh=0.004 mm; after conducting twenty consecutive crimpings, the result was Δh=0.004 mm; and after conducting twenty five consecutive crimpings, the result was Δh=0.005 mm. When observing the hold portion 57 formed after conducting twenty-five consecutive crimpings, the C.H. of the hold portion 57 is lower than that of the hold portion 97 shown in FIG. 12. Further, no gap was observed between the lead core wires 16 enclosed by the bottom portion 57a and the side portions 57b (refer to FIG. 10). Furthermore, the thickness of W1 and W2 did not change, and no burr was produced at the point K.

Next, the result of test 2 will be examined. Since the slidability between the sliding face of the crimper 121 and the outer surface of the U-shaped hold portion 77 was secured by the Ag plating layer 85, despite the increase in the number of crimping operations, the front end sides 77c of the side portions 77b of the U-shaped hold portion 77 penetrated the plurality of lead core wires 16. Thus, the C.H. of the hold portion 57 did not change. Further, it was apparent that the hold portion 57 formed after conducting twenty-five consecutive crimpings was able to tightly fix the lead core wires 16 because the side portions 57b sufficiently penetrated the lead core wires 16. In addition, the hold portion 57 did not loosen and the appearance of the entire crimp contact 51b was normal. Therefore, even though the crimping process is consecutively conducted, a hold portion 57 holding and tightly fixing the lead core wires 16 may be formed. As a result, the crimp contact 51b without any failure in the appearance thereof can be produced.

Next, a test 3 will be explained. In test 3, a plurality of crimp contacts 71b was prepared in which a plating layer made of Au was applied to the outer surface thereof. Then, similarly to tests 1 and 2, the U-shaped hold portions 77 were subjected to a consecutive crimping test. The C.H. (mm) of the crimped hold portion was measured each time a crimping operation was conducted. A variation of the C.H. from a default value (0 mm) of the C.H. of the hold portion, which was measured at the first crimping, was converted to variation Δh. No lubricant was employed in this evaluation.

Next, the result of test 3 will be explained. As shown in FIG. 13, after conducting three consecutive crimpings, the result was Δh=0.003 mm; after conducting six consecutive crimpings, the result was Δh=0.002 mm; after conducting eleven consecutive crimpings, the result was Δh=0.007 mm; after conducting fifteen consecutive crimpings, the result was Δh=0.004 mm; after conducting twenty consecutive crimpings, the result was Δh=0.009 mm; and after conducting twenty-five consecutive crimpings, the result was Δh=0.007 mm.

Next, the result of test 3 will be examined. Even though the material of the plating layer 85 was altered from Ag to Au, almost the same result as in test 2 was obtained. Therefore, it is seen that the slidability between the sliding face of the crimper 121 and the outer surface of the U-shaped hold portion 77 can also be secured by a plating layer 85 made of Au. Further, no failure in the hold portion 57 having the plating layer 85 made of Au and no failure in the appearance of the crimp contact 51b having the hold portion 57 was observed. Although the Au plating was employed as an example in this test, any metal having ductility and heat resistance can be used.

As explained the above, the gas sensor 1 according to this embodiment includes the crimp contact 51b used for outputting a signal from the sensing portion of the sensor element 6 to an external device. In order to have an electric connection to the lead core wires 16 of the electrical lead for an element 14b that is connected to an external device, the crimp contact 51b includes the barrel portion 53 crimped so as to fix the lead core wires 16 of the electrical lead for an element 14b. The barrel portion 53 comprises three hold portions 57. Further, the hold portion 57 is formed such that the lead core wires 16 of the electrical lead for an element 14b are disposed in the U-shaped hold portion 77 so as to be crimped between the anvil 120 and the crimper 121. Then, in this embodiment, the plating layer 85 is formed on the outer surface of the U-shaped hold portion 77 to thereby secure slidability between the sliding face of the crimper 121 and the outer surface of the U-shaped hold portion 77. Thus, during the crimping step of the U-shaped hold portion 77, the front end sides 77c can smoothly slide along the sliding face of the crimper 121 via the plating layer 85. Therefore, the front end sides 77c are deeply bent as an arc toward the bottom portion 77a side so that the lead core wires 16 may be tightly fixed by the bottom portion 77a and the side portions 77b.

Moreover, because slidability is secured between the sliding face of the crimper 121 and the outer surface of the U-shaped hold portion 77, the outer surface of the U-shaped hold portion 77 does not adhere to the respective sliding faces of the anvil 120 and the crimper 121. Thus, the hold portion 57 can be easily removed from each sliding face and the crimp contact 51b is unlikely to be deformed. Furthermore, when a plurality of U-shaped hold portions 77 is crimped consecutively, the hold portion 57 tightly fixing the lead core wires 16 therein may be formed and a crimp contact 51b not having any failure in its appearance may be produced. This is because slidability is secured between the sliding face of the crimper 121 and the outer surface of the U-shaped hold portion 77.

Since the plating layer 85 formed on the outer surface of the crimp contact 51b is made of Ag or Au plating and has heat resistance, the plating layer 85 does not melt or produce a decomposition gas under a high temperature environment, when the gas sensor 1 is mounted on an exhaust pipe of an automobile or the like. As a result, the electromotive voltage of the gas sensor 1 is not adversely influenced.

Figure 16:
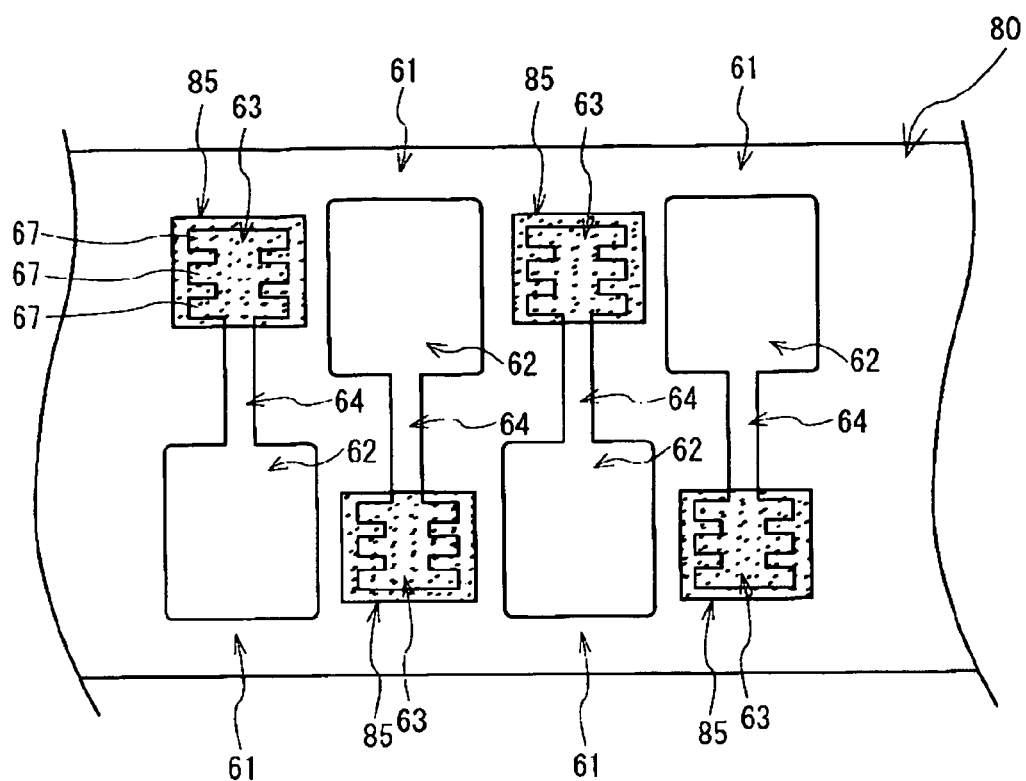
FIG. 16 is a top view of a metal plate 80 to which a partial plating treatment is applied.
Figure 17:
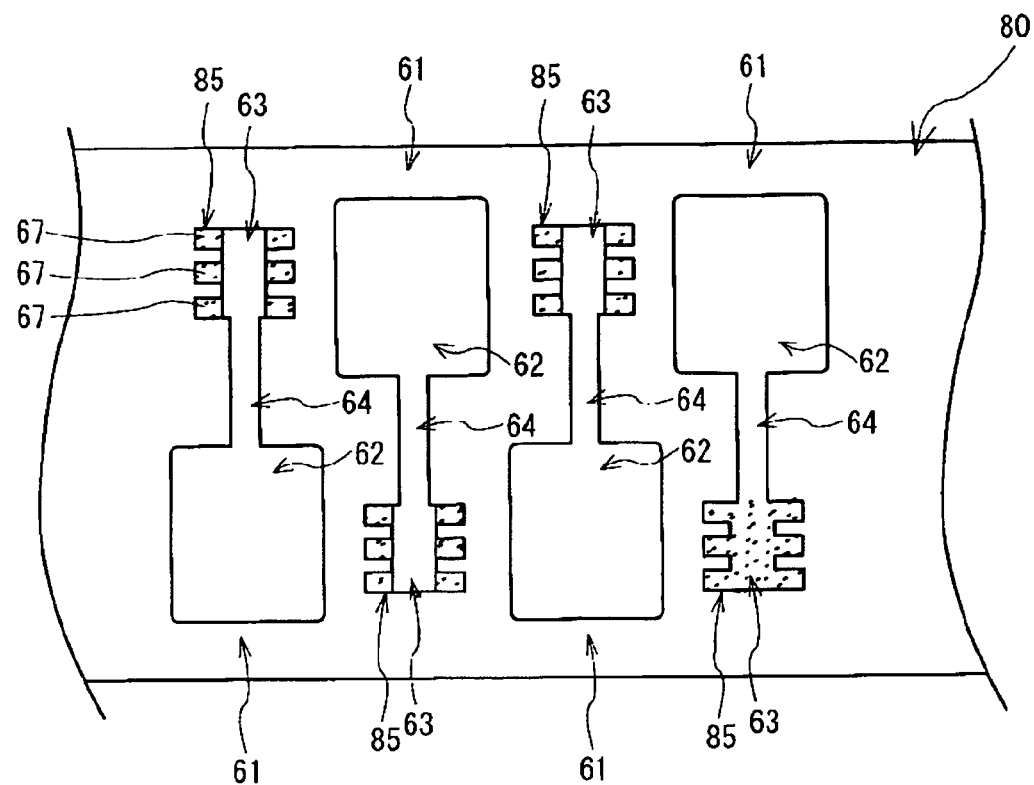
FIG. 17 is a top view of a metal plate 80 to which a partial plating treatment is applied.

The gas sensor according to the present invention is not particularly limited to the embodiments described above but may be changed or modified in various ways within the scope of the invention. For example, in the plating formation process (S10), one side of the metal plate 80 is subjected to the Ag plating in a stripe pattern so that the Ag plating may be applied to the flat barrel portion 63 (three flat hold portions 67). However, as shown in FIG. 16, the Ag plating may be applied partially only to the flat barrel portion 63. By adopting the partial plating, the cost of the plating can be reduced. Further, as shown in FIG. 17, in the barrel portion 63, the plating can be applied to only a portion serving as front end sides of the side portions of the U-shaped hold portion 57. As a result, the cost of the plating can be reduced, while securing slidability between the sliding face of the crimper 121 and the outer surface of the U-shaped hold portion 77.

Further, in the plating process (S10), all the press-mold layouts of the flat terminals 61 formed on the metal plate 80 may be arranged in the same direction. Further, one strip of the plating layer 85 may be formed on the plurality of flat barrel portions 63 disposed in the same side.

Figure 15:
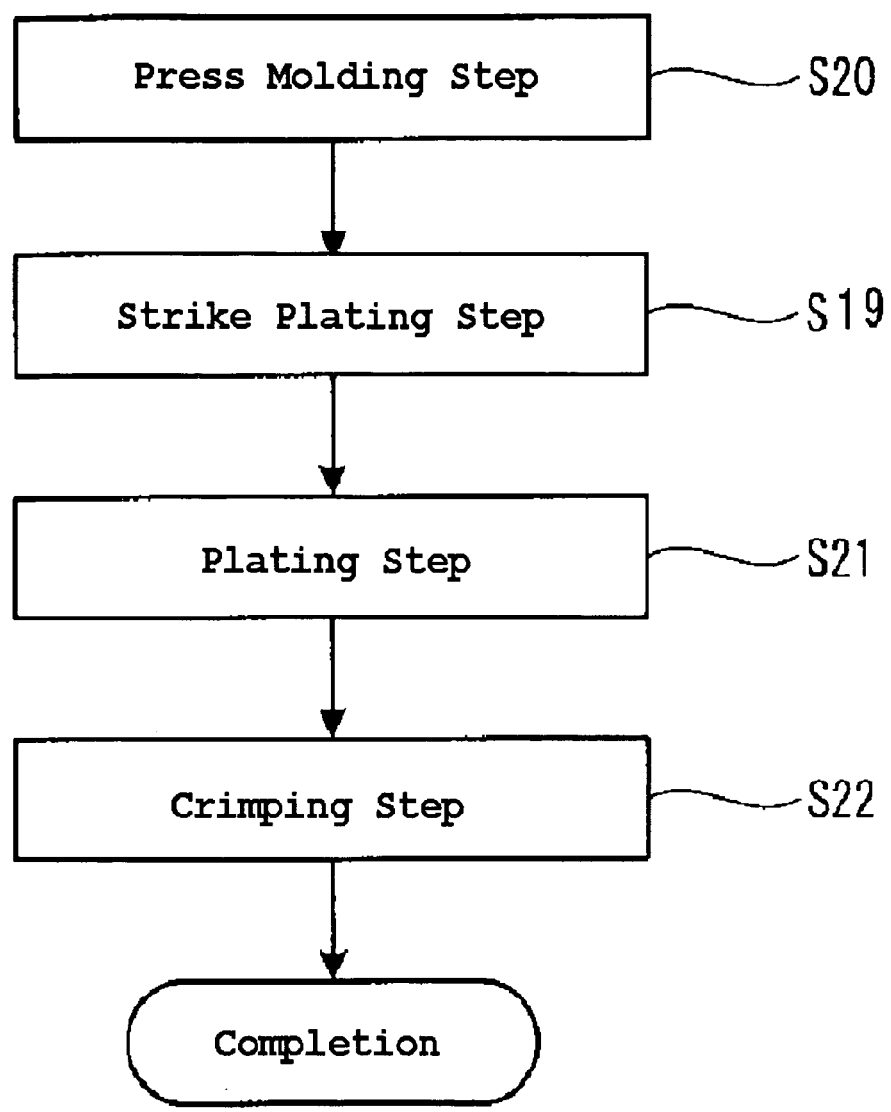
FIG. 15 is a flowchart showing a modification of steps for manufacturing the crimp contact 51b.

As shown in FIG. 4, the manufacturing steps of the crimp contact 51b in this embodiment proceeded in order of the strike plating step (S9), the plating step (S10), the press molding step (S11) and the crimping step (S12). However, as shown in the modification in FIG. 15, the crimp contact 51b may be formed in such order that, for example, a press molding step (S20) may be conducted prior to a strike plating step (S19) where the strike plating is applied only to the U-shaped barrel portion 73 of the thus-press molded crimp contact 71b, and subsequently a plating step (S21) and a crimping step (S22) may be conducted in this order. In these manufacturing steps, the metal plate 80 is press molded in the press molding step, and the crimp contact 71b including the U-shaped hold portion 77 is formed. Then, only the U-shaped barrel portion 73 of the crimp contact 71b is immersed in an Ag plating bath or an Au plating bath with adjusting a plating location by a liquid level control.

The present invention is applicable not only to a gas sensor, such as an oxygen sensor, but also applicable to various devices.

It should further be apparent to those skilled in the art that various changes in form and detail of the invention as shown and described above may be made. It is intended that such changes be included within the spirit and scope of the claims appended hereto.

This application is based on Japanese Patent Application No. 2005-349407 filed Dec. 2, 2005, the disclosure of which is incorporated herein by reference in its entirety.

What is claimed is:

1. A crimp contact, comprising:
   a terminal portion for electrical connection to another member; and
   a hold portion for holding lead core wires of an electrical lead therein so as to be electrically connected to said electrical lead, said hold portion including a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, wherein a metal plating layer comprising Ag or Au as a main component covers at least part of an outer surface of said front end sides of said pair of side portions, and the front end sides have a thickness greater than that of the metal plating layer, and wherein:

the pair of side portions rises from both ends of the bottom portion, when viewed in a cross section perpendicular to the axial direction;

the front end sides of the side portions located opposed to the bottom portion thereof are bent toward the bottom portion;

an outer surface of one of the front end sides is in contact with an outer surface of the other front end side;

the lead core wires are disposed, when viewed in a cross section perpendicular to the axial direction, in an opening formed by the entire inner surface of each of the side portions and an inner surface of the bottom portion; and at least one or more lead core wires is sandwiched by at least the inner surface of one of the side portions, wherein an inner surface of the hold portion, which has a Vickers hardness of 350 HV or more when measured at the inner surface of the hold portion, is in direct contact with the at least one or more lead core wires.

2. The crimp contact as claimed in claim 1, wherein said metal plating layer has a Vickers hardness of 100 HV or less.

3. The crimp contact as claimed in claim 1, wherein said metal plating layer has a thickness of 0.1 μm or more.

4. The crimp contact as claimed in claim 1, wherein a strike plating layer including Au as a main component is formed between said metal plating layer and said outer surface of said front end sides of said pair of side portions.

5. The crimp contact as claimed in claim 1, wherein said metal plating layer is continuously formed on said outer surfaces of said front end sides of said pair of side portions.

6. A crimp contact with an electrical lead, comprising:

an electrical lead including lead core wires and a cover member exposing said lead core wires from one end thereof; and a crimp contact including a terminal portion for electrical connection to another member and a hold portion holding said lead core wires of said electrical lead therein so as to be electrically connected to said electrical lead, said hold portion including a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, wherein a metal plating layer including Ag or Au as a main component covers at least part of an outer surface of said front end sides of said pair of side portions, and the front end sides have a thickness greater than that of the metal plating layer, and wherein:

the pair of side portions rises from both ends of the bottom portion, when viewed in a cross section perpendicular to the axial direction;

the front end sides of the side portions located opposed to the bottom portion thereof are bent toward the bottom portion;

an outer surface of one of the front end sides is in contact with an outer surface of the other front end side;

the lead core wires are disposed, when viewed in a cross section perpendicular to the axial direction, in an opening formed by the entire inner surface of each of the side portions and an inner surface of the bottom portion; and at least one or more lead core wires is sandwiched by at least the inner surface of one of the side portions, wherein an inner surface of the hold portion, which has a Vickers hardness of 350 HV or more when measured at the inner surface of the hold portion, is in direct contact with the at least one or more lead core wires.

7. The crimp contact with an electrical lead as claimed in claim 6, wherein said metal plating layer has a Vickers hardness of 100 HV or less.

8. The crimp contact with an electrical lead as claimed in claim 6, wherein said metal plating layer has a thickness of 0.1 μm or more.

9. The crimp contact with an electrical lead as claimed in claim 6, wherein a strike plating layer including Au as a main component is formed between said metal plating layer and said outer surface of said front end sides of said pair of side portions.

10. The crimp contact with an electrical lead as claimed in claim 6, wherein said metal plating layer is continuously formed on said outer surfaces of said front end sides of said pair of side portions.

11. A gas sensor, comprising:

a sensor element extending in an axial direction and including a sensing portion at a front end side thereof;

a cylindrical metal housing which holds said sensor element so that at least said sensing portion is exposed from a front end side of said metal housing;

a protective cover including a front end connected to a rear end side of said metal housing, said protective cover accommodating therein at least one electrical lead for electrical connection to an external device;

said electrical lead including lead core wires and a cover member exposing said lead core wires at one end thereof; and a crimp contact electrically connecting said sensor element to said electrical lead and adapted for outputting a signal from said sensing portion to an external device, wherein said crimp contact includes:

a terminal portion for electrical connection to said sensor element and a hold portion holding said lead core wires of said electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions, wherein said hold portion has a Vickers hardness of 350 HV or more, wherein a metal plating layer including Ag or Au as a main component covers at least part of an outer surface of said front end sides of said pair of side portions, and the front end sides have a thickness greater than that of the metal plating layer, and wherein:

the pair of side portions rises from both ends of the bottom portion, when viewed in a cross section perpendicular to the axial direction;

the front end sides of the side portions located opposed to the bottom portion thereof are bent toward the bottom portion;

an outer surface of one of the front end sides is in contact with an outer surface of the other front end side;

the lead core wires are disposed, when viewed in a cross section perpendicular to the axial direction, in an opening formed by the entire inner surface of each of the side portions and an inner surface of the bottom portion; and at least one or more lead core wires is sandwiched by at least the inner surface of one of the side portions, wherein an inner surface of the hold portion, which has a Vickers hardness of 350 HV or more when measured at the inner surface of the hold portion, is in direct contact with the at least one or more lead core wires.

12. The gas sensor as claimed in claim 11, wherein said metal plating layer has a Vickers hardness of 100 HV or less.

13. The gas sensor as claimed in claim 11, wherein said metal plating layer has a thickness of 0.1 µm or more.

14. The gas sensor as claimed in claim 11, wherein a strike plating layer including Au as a main component is formed between said metal plating layer and said outer surface of said front end sides of said pair of side portions.

15. The gas sensor as claimed in claim 11, wherein said metal plating layer is continuously formed on said outer surfaces of said front end sides of said pair of side portions.

16. A method for manufacturing a gas sensor, said gas sensor comprising:

a sensor element extending in an axial direction and including a sensing portion at a front end side thereof;

a cylindrical metal housing which holds said sensor element so that at least said sensing portion is exposed from a front end side of said metal housing;

a protective cover including a front end connected to a rear end side of said metal housing, said protective cover accommodating therein at least one electrical lead for electrical connection to an external device;

said electrical lead including lead core wires and a cover member exposing said lead core wires at one end thereof; and a crimp contact electrically connecting said sensor element to said electrical lead and adapted for outputting a signal from said sensing portion to an external device, wherein said crimp contact includes:

a terminal portion for electrical connection to another member; and a hold portion holding said lead core wires of said electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions, and wherein:

the pair of side portions rises from both ends of the bottom portion, when viewed in a cross section perpendicular to the axial direction;

the front end sides of the side portions located opposed to the bottom portion thereof are bent toward the bottom portion;

an outer surface of one of the front end sides is in contact with an outer surface of the other front end side;

the lead core wires are disposed, when viewed in a cross section perpendicular to the axial direction, in an opening formed by the entire inner surface of each of the side portions and an inner surface of the bottom portion; and at least one or more lead core wires is sandwiched by at least the inner surface of one of the side portions, wherein an inner surface of the hold portion, which has a Vickers hardness of 350 HV or more when measured at the inner surface of the hold portion, is in direct contact with the at least one or more lead core wires, said method comprising:

forming a metal plating layer covering at least a portion of one surface of a metal plate which is to become said front end sides of said side portions, said metal plating layer including Ag or Au as a main component, and the front end sides have a thickness greater than that of the metal plating layer;

press molding said metal plate so as to form a U-shaped hold portion including said pair of side portions and said bottom portion so that said one surface of said metal plate is an outer surface; and disposing said lead core wires in said U-shaped hold portion and bending said side portions by a pair of an anvil and a crimper so that said hold portion crimps said lead core wires, and wherein said metal plate has a Vickers hardness of 350 HV or more.

17. The method for manufacturing a gas sensor as claimed in claim 16, further comprising:

applying an Au strike plating so as to cover at least a portion on one surface of said metal plate which is to become said front end sides of said side portions, wherein said Au strike plating applying step is performed prior to said forming the metal plating layer step.

18. A method for manufacturing a gas sensor, wherein said gas sensor comprises:

a sensor element extending in an axial direction and including a sensing portion at a front end side thereof;

a cylindrical metal housing which holds said sensor element so that at least said sensing portion is exposed from a front end side of said metal housing;

a protective cover including a front end connected to a rear end side of said metal housing, said protective cover accommodating therein at least one electrical lead for electrical connection to an external device;

said electrical lead including lead core wires and a cover member exposing said lead core wires at one end thereof; and a crimp contact electrically connecting said sensor element to said electrical lead and adapted for outputting a signal from said sensing portion to an external device, wherein said crimp contact includes:

a terminal portion for electrical connection to another member; and a hold portion holding lead core wires of an electrical lead therein so as to be electrically connected to said electrical lead, wherein said hold portion includes a pair of side portions for fixing said lead core wires by bending front end sides thereof toward said lead core wires of said electrical lead and a bottom portion connecting a rear end side of said pair of side portions, and wherein:

the pair of side portions rises from both ends of the bottom portion, when viewed in a cross section perpendicular to the axial direction;

the front end sides of the side portions located opposed to the bottom portion thereof are bent toward the bottom portion;

an outer surface of one of the front end sides is in contact with an outer surface of the other front end side;

the lead core wires are disposed, when viewed in a cross section perpendicular to the axial direction, in an opening formed by the entire inner surface of each of the side portions and an inner surface of the bottom portion; and at least one or more lead core wires is sandwiched by at least the inner surface of one of the side portions, wherein an inner surface of the hold portion, which has a Vickers hardness of 350 HV or more when measured at the inner surface of the hold portion, is in direct contact with the at least one or more lead core wires, wherein said method comprises:

press molding a metal plate to form an U-shaped hold portion including said pair of side portions and said bottom portion, said metal plate having a Vickers hardness of 350 HV or more;

forming a metal plating layer covering at least part of an outer surface of said front end sides of said side portions of said U-shaped hold portion, wherein the front end sides have a thickness greater than that of the metal plating layer; and disposing said lead core wires in said U-shaped hold portion and bending said pair of side portions by a pair of an anvil and a crimper so that said hold portion crimps said lead core wires.

19. The method for manufacturing a gas sensor as claimed in claim 18, comprising:

applying an Au strike plating so as to cover at least a portion on one surface of said metal plate which is to become said front end sides of said side portions, and wherein said Au strike plating applying step is carried out between said press molding step and said forming the metal plating layer step.

\* \* \* \* \*